(12) United States Patent
Kim et al.

(10) Patent No.: US 10,014,479 B2
(45) Date of Patent: Jul. 3, 2018

(54) ORGANIC LIGHT-EMITTING DIODE WITH HIGH EFFICIENCY AND LONG LIFETIME

(71) Applicant: SFC CO., LTD., Chungcheongbuk-do (KR)

(72) Inventors: Hee-Dae Kim, Gyeongsangnam-do (KR); Seok-Bae Park, Chungcheongnam-do (KR); Yoona Shin, Seoul (KR); Sang-Woo Park, Seoul (KR); Soon-Wook Cha, Gyeonggi-do (KR)

(73) Assignee: SFC CO., LTD., Chungcheongbuk-Do (KR)

( * ) Notice: Subject to any disclaimer, the term of this patent is extended or adjusted under 35 U.S.C. 154(b) by 158 days.

(21) Appl. No.: 14/981,659

(22) Filed: Dec. 28, 2015

(65) Prior Publication Data
US 2016/0204355 A1   Jul. 14, 2016

(30) Foreign Application Priority Data

Jan. 13, 2015   (KR) .................. 10-2015-0004537

(51) Int. Cl.
*H01L 51/00* (2006.01)
*H01L 27/32* (2006.01)
(Continued)

(52) U.S. Cl.
CPC ........ *H01L 51/0061* (2013.01); *C07C 211/54* (2013.01); *C07C 211/55* (2013.01); *C07C 211/59* (2013.01); *C07C 211/60* (2013.01); *C07C 211/61* (2013.01); *C07D 307/77* (2013.01); *C07D 307/91* (2013.01); *C07D 405/14* (2013.01); *C07D 493/04* (2013.01); *C07D 493/10* (2013.01); *C07F 7/0812* (2013.01); *C09K 11/06* (2013.01); *H01L 27/3244* (2013.01); *H01L 51/006* (2013.01); *H01L 51/0052* (2013.01); *H01L 51/0054* (2013.01); *H01L 51/0058* (2013.01); *H01L 51/0059* (2013.01); *H01L 51/0072* (2013.01); *H01L 51/0073* (2013.01); *H01L 51/0074* (2013.01); *H01L 51/0094* (2013.01); *C09K 2211/1007* (2013.01); *C09K 2211/1011* (2013.01); *C09K 2211/1014* (2013.01); *C09K 2211/1088* (2013.01); *H01L 51/0002* (2013.01); *H01L 51/504* (2013.01); *H01L 51/5016* (2013.01)

(58) Field of Classification Search
None
See application file for complete search history.

(56) References Cited

U.S. PATENT DOCUMENTS

2017/0062729 A1* 3/2017 Cha .................. H01L 51/0094

FOREIGN PATENT DOCUMENTS

| KR | 10-2008-0015865 A | 2/2008 |
| KR | 10-2011-0015213 A | 2/2011 |

(Continued)

*Primary Examiner* — Sin J Lee
(74) *Attorney, Agent, or Firm* — The PL Law Group, PLLC

(57) ABSTRACT

An organic light-emitting diode with high efficiency and long lifetime includes a first electrode, a second electrode facing the first electrode and an emissive layer between the first electrode and the second electrode, wherein the emissive layer includes a luminescent material that allows for the emission of deep blue light at high efficiency with a long lifetime.

17 Claims, 4 Drawing Sheets

(51) Int. Cl.

| | |
|---|---|
| *C07C 211/61* | (2006.01) |
| *C07C 211/60* | (2006.01) |
| *C07C 211/59* | (2006.01) |
| *C07C 211/55* | (2006.01) |
| *C07C 211/54* | (2006.01) |
| *C07D 307/91* | (2006.01) |
| *C07D 307/77* | (2006.01) |
| *C07D 493/04* | (2006.01) |
| *C07D 493/10* | (2006.01) |
| *C07D 405/14* | (2006.01) |
| *C07F 7/08* | (2006.01) |
| *C09K 11/06* | (2006.01) |
| *H01L 51/50* | (2006.01) |

(56) References Cited

FOREIGN PATENT DOCUMENTS

| | | |
|---|---|---|
| KR | 10-2012-0047706 A | 5/2012 |
| WO | WO 2015/174682 A1 * | 11/2015 |
| WO | WO 2016/013184 A1 * | 1/2016 |
| WO | WO 2016/079944 A1 * | 5/2016 |
| WO | WO 2016/088759 A1 * | 6/2016 |
| WO | WO 2016/104289 A1 * | 6/2016 |

\* cited by examiner

ORGANIC LIGHT-EMITTING DIODE WITH HIGH EFFICIENCY AND LONG LIFETIME

CROSS-REFERENCE TO RELATED APPLICATION AND CLAIM OF PRIORITY

The application claims the benefits of the Korean Patent Application No. 10-2015-0004537 filed on Jan. 13, 2015 at Korean Intellectual Property Office, the disclosure of which is incorporated herein in its entirety by reference.

BACKGROUND

1. Field of the Invention

The present invention relates to an organic light-emitting diode with high efficiency and a long lifetime. More particularly, the present invention relates to an organic light-emitting diode that can emit deep blue light as well as having high efficiency and a long lifetime.

2. Description of the Related Art

Organic light emitting diodes (OLEDs), based on self-luminescence, are used to create digital displays with the advantage of being able to be thinner and lighter than liquid crystal displays (LCDs). In addition, an OLED display exhibits a much faster response time than an LCD. Accordingly, organic light emitting diodes find applications in the illumination field as well as the full-color display field.

Materials used as the organic layers in organic light emitting diodes may be divided into luminescent materials and charge carrier materials, for example, a hole injection material, a hole transport material, an electron injection material, and an electron transport material. According to the luminescent materials, there are two main families of OLED: those based on small molecules and those employing polymers. The light emitting mechanisms allows the luminescent materials to be classified as fluorescent and phosphorescent materials, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emitting efficiency. In this regard, a host-dopant system may be used as a luminescent material so as to increase the color purity and the light emitting efficiency through energy transfer.

This is based on the principle that, when a dopant is smaller in energy band gap than a host accounting for the emissive layer, the addition of a small amount of the dopant to the host generates excitons from the emissive layer so that the excitons are transported to the dopant, emitting light at high efficiency. Here, light of desired wavelengths can be obtained depending on the kind of the dopant because the wavelength of the host moves to a wavelength range of the dopant.

With regard to related arts of dopant compounds in the emissive layer, reference may be made to Korean Patent Unexamined Application Publication No. 10-2008-0015865 (Feb. 20, 2008), which describes an organic light emitting device using an arylamine-coupled indenofluorene derivative, and Korean Patent Unexamined Application Publication No. 10-2012-0047706 (May 14, 2012), which describes an organic photoelectric device using a compound in which dibenzofuran or dibenzothiophene coexists with fluorene or carbazole.

In recent years, studies have been conducted on organic light emitting compounds having high efficiency and a long lifetime, and are ongoing particularly on organic light-emitting diodes using blue light-emitting compounds having high efficiency and a long lifetime.

As a related art for an organic light-emitting diode using a blue light-emitting compound, mention may be made of Korean Patent Unexamined Application Publication No. 10-2011-0015213 (Jan. 15, 2011) in which pyrene arylamine derivatives with various substituents on the aryl moiety are used for organic light-emitting diodes.

Given a CIE of 0.1 or less for deep blue, however, most of the pyrene derivatives are poor in efficiency and have a short lifetime. Despite various efforts made to solve the problems, there is still continuation of a need for the development of a novel organic light-emitting diode that exhibits higher efficiency and a longer lifetime than conventional organic light-emitting diodes.

SUMMARY

Therefore, an aspect of the present disclosure aims to provide a novel organic light-emitting diode (OLED) with high efficiency and a long lifetime.

Also, the present disclosure aims to provide an OLED with which a display can be fabricated at a small thickness and with a wide viewing angle.

In accordance with an aspect thereof, the present disclosure provides an organic light-emitting diode, comprising: a first electrode; a second electrode facing the first electrode; an emissive layer intercalated between the first electrode and the second electrode, wherein the emissive layer comprises at least one of the amine compounds represented by the following Chemical Formula A, and emits light with a color coordinate CIEy on a chromaticity diagram of 0.1 or less.

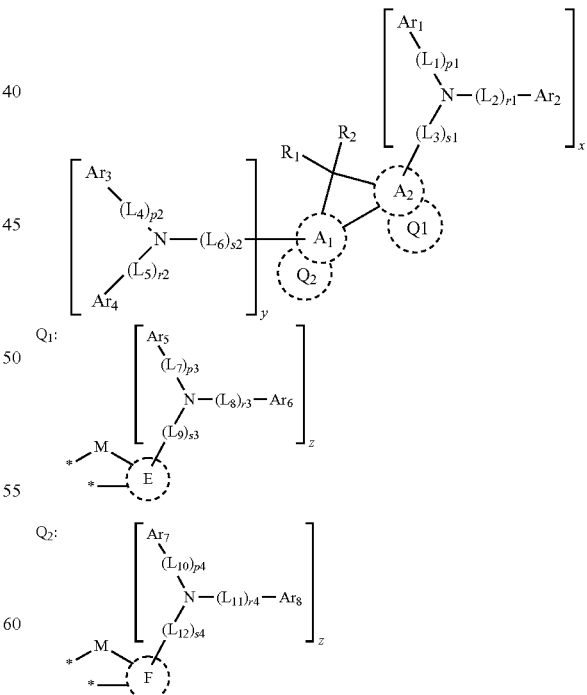

[Chemical Formula A]

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substitutents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among $N-R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with a proviso that $R_1$ and $R_2$ together may form a mono- or polycyclic aliphatic or aromatic ring that may be a heterocyclic ring with a heteroatom selected from among N, O, P, Si, S, Ge, Se, and Te as a ring member;

p1 to p4, r1 to r4, and s1 to s4 are each independently an integer of 1 to 3, with a proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_1$ ring occupying respective positions * of Structural Formula $Q_2$ to form a fused ring, two adjacent carbon atoms of the $A_2$ ring occupying respective positions * of structural Formula $Q_1$ to form a fused ring, the term 'substituted' in the expression 'substituted or unsubstituted' meaning having a substituent selected from the group consisting of deuterium, cyano, halogen, hydroxy, nitro, alkyl of 1 to 24 carbon atoms, halogenated alkyl of 1 to 24 carbon atoms, alkenyl of 2 to 24 carbon atoms, alkynyl of 2 to 24 carbon atoms, heteroalkyl of 1 to 24 carbon atoms, aryl of 6 to 24 carbon atoms, arylalkyl of 7 to 24 carbon atoms, heteroaryl of 2 to 24 carbon atoms or heteroarylalkyl of 2 to 24 carbon atoms, alkoxy of 1 to 24 carbon atoms, alkylamino of 1 to 24 carbon atoms, arylamino of 6 to 24 carbon atoms, hetero arylamino of 1 to 24 carbon atoms, alkylsilyl of 1 to 24 carbon atoms, arylsilyl of 6 to 24 carbon atoms, and aryloxy of 6 to 24 carbon atoms.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
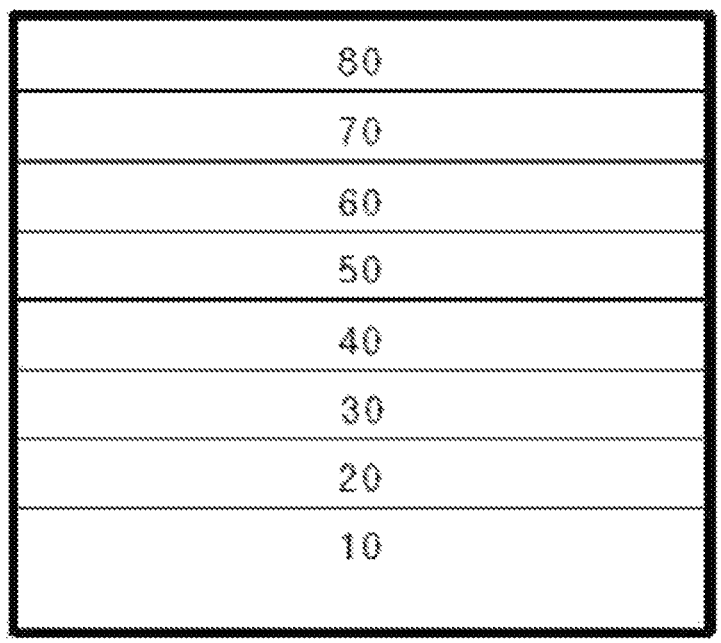
FIG. 1 is a schematic cross-sectional view of the structure of an organic light-emitting diode according to some embodiments of the present disclosure.

In accordance with an aspect thereof, the present disclosure addresses an organic light-emitting diode, comprising a first electrode; a second electrode facing the first electrode; an emissive layer intercalated between the first electrode and the second electrode, wherein the emissive layer comprises at least one of amine compounds represented by the following Chemical Formula A and emits light with a color coordinate CIEy on a chromaticity diagram of 0.1 or less.

The expression for a number of carbon atoms such as in "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an aromatic system including a least one ring. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom on which may be substituted by a deuterium atom, a halogen atom, hydroxy, nitro, cyano, silyl, amino ($-NH_2$, $-NH(R)$, $-N(R')(R'')$ wherein R' and R" are each independently an alkyl of 1 to 10 alkyl, in this case, called "alkylamino"), amidino, hydrazine, hydrazone, carboxyl, sulfonic acid, phosphoric acid, alkyl of 1 to 24 carbon atoms, halogenated alkyl of 1 to 24 carbon atoms, alkenyl of 1 to 24 carbon atoms, alkynyl of 1 to 24 carbon atoms, heteroalkyl of 1 to 24 carbon atoms, aryl of 6 to 24 carbon atoms, arylalkyl of 7 to 24 carbon atoms, heteroaryl of 2 to 24 carbon atoms, or heteroarylalkyl of 2 to 24 carbon atoms.

The substituent heteroaryl used in the compound of the present invention refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present invention are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. One or more hydrogen atom of the silyl may be substituted by the same substituent as in the aryl.

The compound of Chemical Formula A used in the present disclosure is characterized by the structure in which the moieties of Chemical Formulas $Q_2$ and $Q_1$ are respectively connected to the rings $A_1$ and $A_2$ while an amine moiety containing both $Ar_1$ and $Ar_2$ is bonded to the ring $A_2$.

According to some embodiments of the present disclosure, $A_1$, $A_2$, E, and F in Chemical Formula A may be the same or different and may be each independently a substituted or unsubstituted aromatic hydrocarbon ring of 6 to 50 carbon atoms.

When $A_1$, $A_2$, E, and F in Chemical Formula A are each independently a substituted or unsubstituted aromatic hydrocarbon ring of 6 to 50 carbon atoms, the aromatic hydrocarbon ring moieties may be each independently any one selected from among [Structural Formula 10] to [Structural Formula 21].

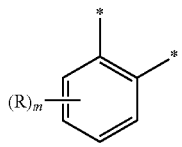

[10]

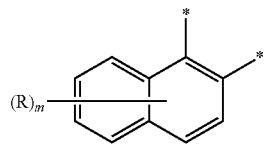

[11]

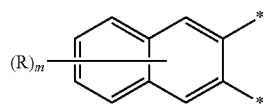

[12]

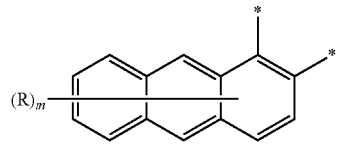

[13]

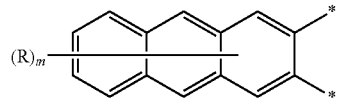

[14]

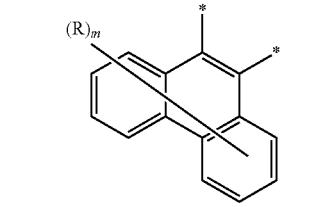

[15]

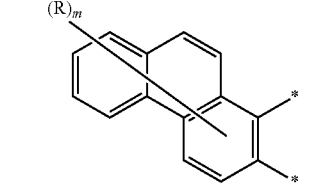

[16]

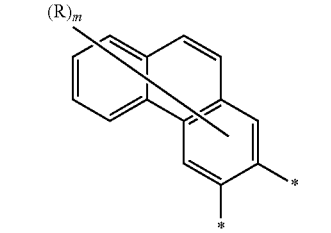

[17]

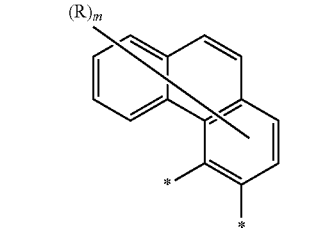

[18]

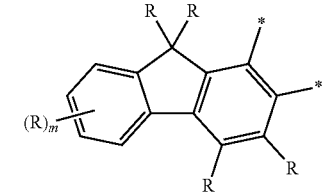

[19]

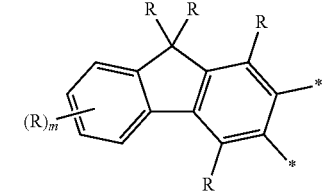

[20]

[21]

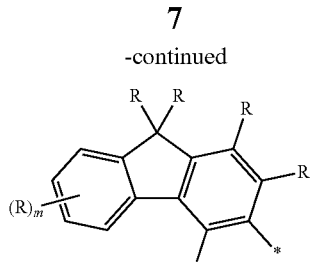

wherein,

"-*" for moiety $A_1$ or $A_2$ denotes a bonding site for forming a 5-membered ring containing the carbon atom connected to both the substituents $R_1$ and $R_2$, and "-*" for moiety E or F denotes a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R is the same as above defined for $R_1$ and $R_2$, m is an integer of 1 to 8, with a proviso that when m is 2 or greater, or R is 2 or greater, the corresponding Rs may be the same or different.

In some embodiments of the present disclosure, $A_1$, $A_2$, E, and F in Chemical Formula A may be the same or different and may be each independently a substituted or unsubstituted heteroaromatic ring of 2 to 30 carbon atoms.

As described above, when $A_1$, $A_2$, E, F in Chemical Formula A may be the same or different and are each independently a substituted or unsubstituted heteroaromatic ring of 2 to 30 carbon atoms, the heteroaromatic ring may be the same or different and may be independently any one selected from among [Structural Formula 31] to [Structural Formula 40].

[31]

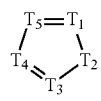

[32]

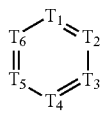

[33]

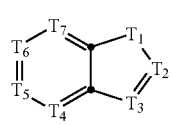

[34]

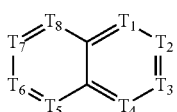

[35]

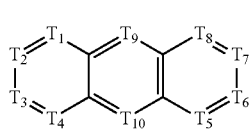

[36]

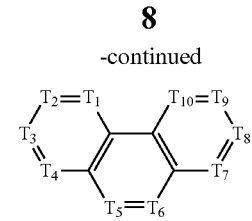

[37]

[38]

[39]

[40]

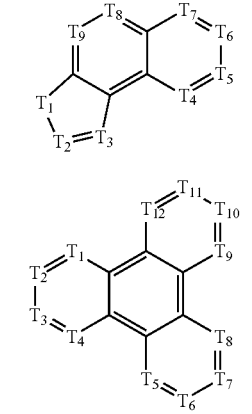

wherein, $T_1$ to $T_{12}$ may be the same or different and may each be independently any one selected from among $C(R_{41})$, $C(R_{42})(R_{43})$, N, $N(R_{44})$, O, S, Se, Te, $Si(R_{45})(R_{46})$, and $Ge(R_{47})(R_{48})$, with the exclusion of all members Ts in each of the rings Ts being carbon atoms, $R_{41}$ to $R_{48}$ are the same as above defined for $R_1$ and $R_2$, an adjacent two of the aromatic ring members $T_1$ to $T_{12}$ for moiety $A_1$ or $A_2$ are carbon atoms forming a 5-membered ring containing the carbon atom connected to both the substituents $R_1$ and $R_2$, and an adjacent two of the aromatic ring members $T_1$ to $T_{12}$ for moiety E or F are carbon atoms forming a 5-membered ring containing M of the structural Formula $Q_1$ and $Q_2$ with the moiety $A_1$ or $A_2$, when one of the hetero aromatic rings of [Structural Formula 31] to [Structural Formula 40] for $A_1$ or $A_2$ is bonded to Structural Formula $Q_1$ or Structural Formula $Q_2$, the adjacent two of the aromatic ring members $T_1$ to $T_{12}$ are carbon atoms and occupy respective positions * of Structural Formula $Q_1$ or $Q_2$ to form a fused ring.

In some particular embodiments, the heteroaromatic rings represented by [Structural Formula 31] to [Structural Formula 40] may be selected from heterorings represented by the following [Structural Formula 41]:

[Structural Formula 41]

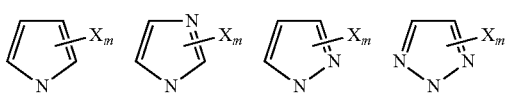

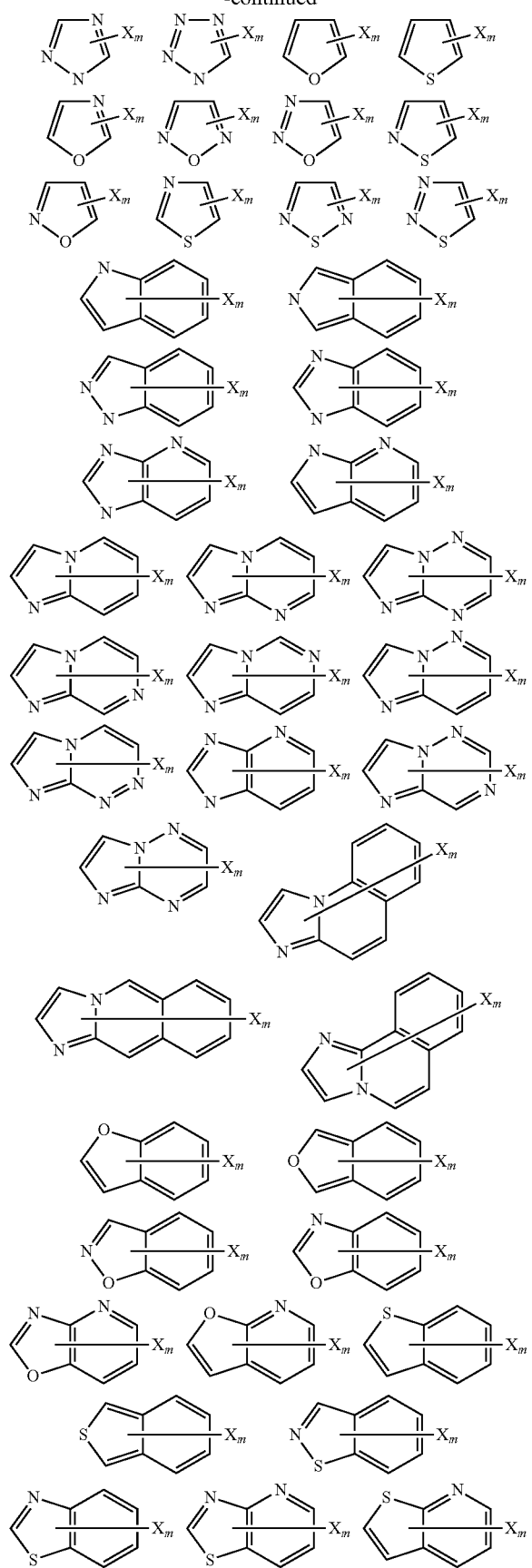
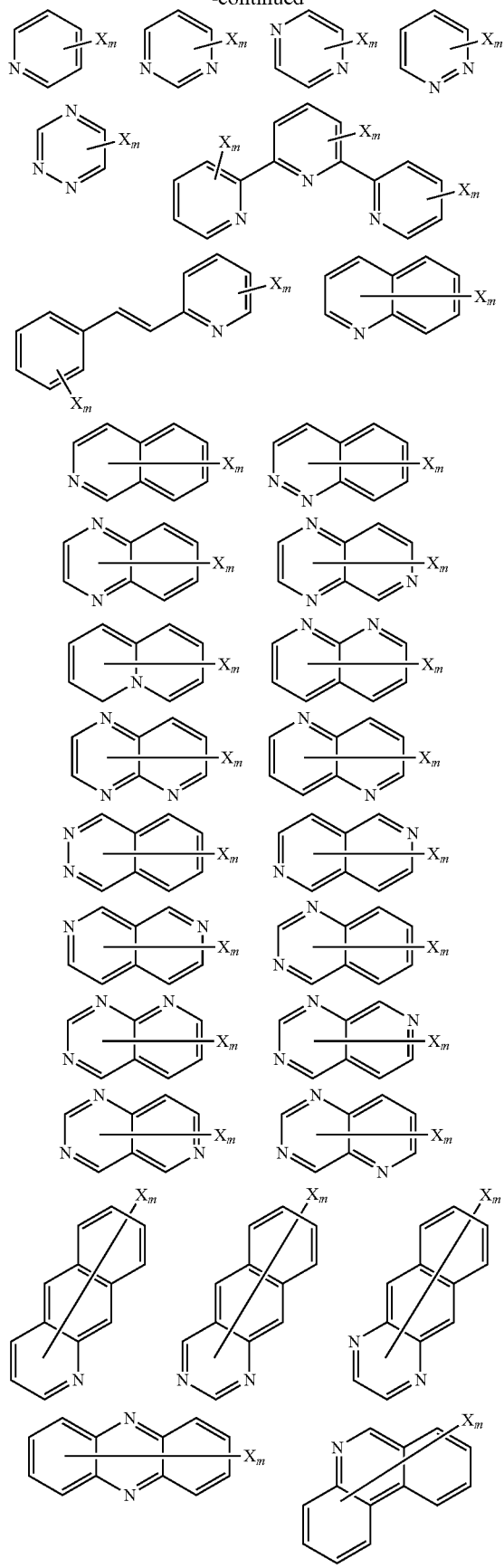

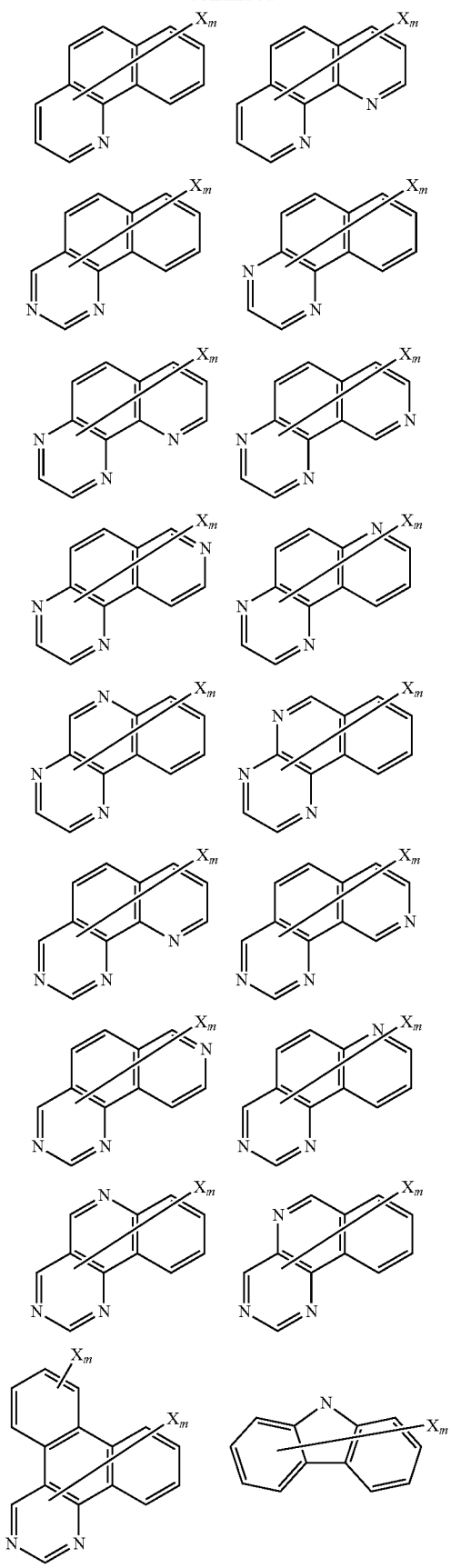
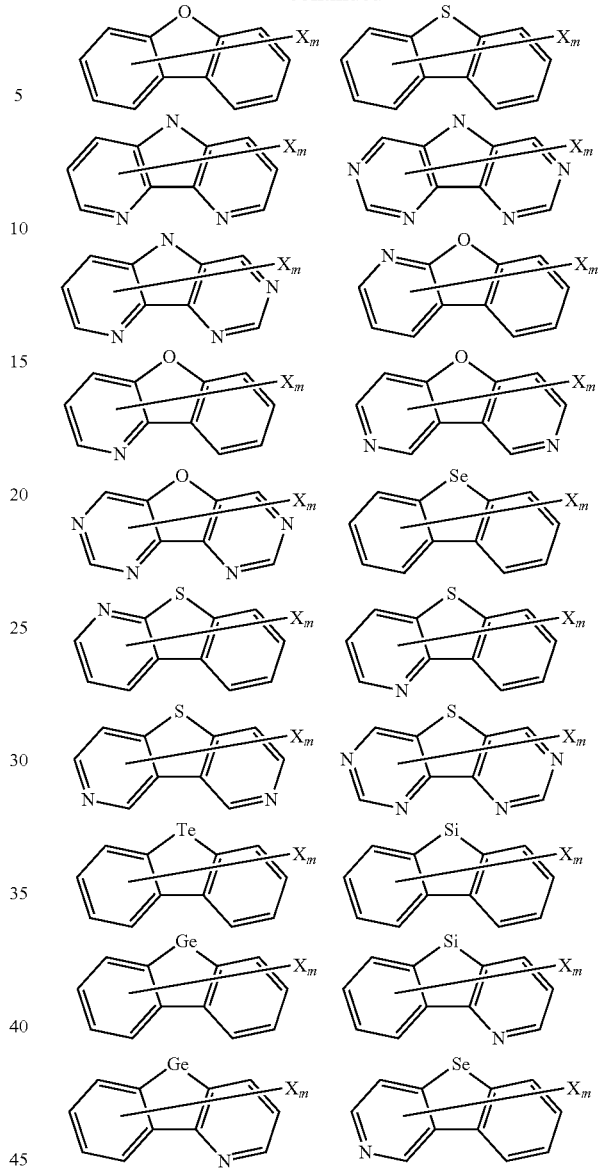

wherein,

X is the same as above defined for $R_1$ and $R_2$, m is an integer of 1 to 11, with a proviso that when m is 2 or greater, the corresponding Xs may be the same or different.

In [Structural Formula 41], the adjacent two carbon atoms of each of the aromatic rings for $A_1$ or $A_2$ forms a 5-membered ring containing the carbon atom connected to both the substituents $R_1$ and $R_2$, and the adjacent two of the aromatic rings for moiety E or F are carbon atoms forming a 5-membered ring containing M of the structural Formula $Q_1$ and $Q_2$ with the moiety $A_1$ or $A_2$, when one of the aromatic hydrocarbon rings of [Structural Formula 41] for $A_1$ or $A_2$ is bonded to Structural Formula $Q_1$ or Structural Formula $Q_2$, two adjacent carbon atoms of the aromatic ring occupy respective positions * of Structural Formula $Q_1$ or $Q_2$ to form a fused ring.

According to some embodiments of the present disclosure, linkers $L_1$ to $L_{12}$ in Chemical Formula A may be a direct bond, or any one selected from among a substituted or unsubstituted arylene of 6 to 20 carbon atoms and a substituted or unsubstituted heteroarylene of 2 to 20 carbon atoms.

In a particular embodiment, linkers $L_1$ to $L_{12}$ may be a direct bond, or any one selected from the following [Structural Formula 22] to [Structural Formula 30], p1 to p4, r1 to r4, and s1 to s4 may each be 1 or 2, and x may be 1:

[22] 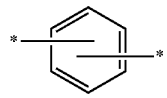

[23] 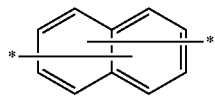

[24] 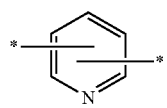

[25] 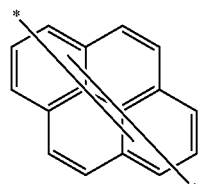

[26] 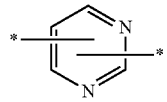

[27] 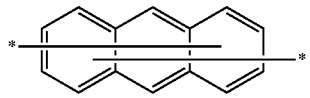

[28] 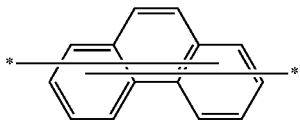

[29] 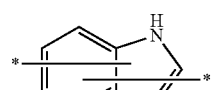

[30] 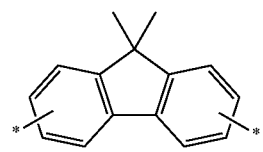

On a carbon atom as a member of the aromatic ring of the linker, hydrogen or deuterium may be positioned.

In a specific embodiment of the present disclosure, y may be 1, and z is 0.

In Chemical Formula A according to some embodiments of the present disclosure, $R_1$ and $R_2$, which may be the same or different, are each independently a substituted or unsubstituted aryl of 6 to 24 carbon atoms, and may or may not be bonded to each other to form a ring.

In a specific embodiment of the present disclosure, $R_1$ to $R_9$, and $Ar_1$ to $Ar_8$ may be the same or different and may each be independently any one selected from among hydrogen, deuterium, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms containing at least one heteroatom selected from among O, N, S, and Si, a cyano, and a halogen.

In the amine moieties of Chemical Formula A according to some embodiments of the present disclosure, $A_1$, $A_2$, E, F, $Ar_1$ to $Ar_8$, $L_1$ to $L_{12}$, $R_1$ to $R_9$ may have as a substituent any one selected from the group consisting of a cyano, a halogen, an alkyl of 1 to 6 carbon atoms, an aryl of 6 to 18 carbon atoms, an arylalkyl of 7 to 18 carbon atoms, a heteroaryl of 3 to 18 carbon atoms, an alkylsilyl of 1 to 12 carbon atoms, and an arylsilyl of 6 to 18 carbon atoms.

The amine compound represented by Chemical Formula A, useful in the organic light-emitting diode of the present disclosure, may be selected from compounds represented by the following [Chemical Formula 1] to [Chemical Formula 21].

<1>

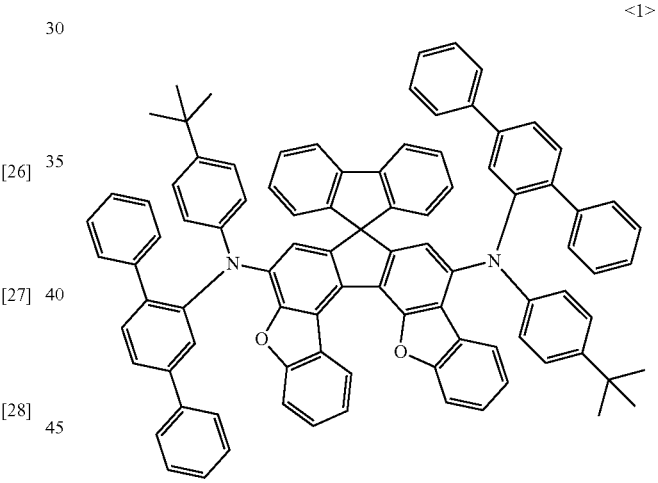

<2>

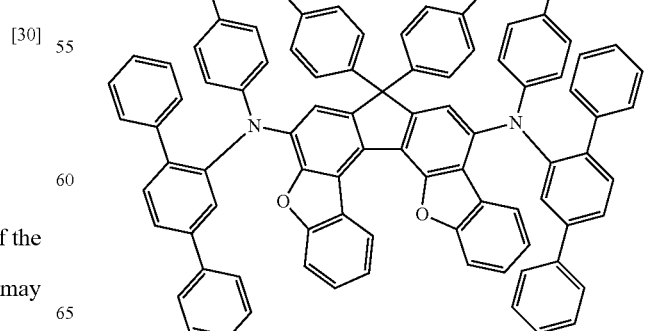

<3>
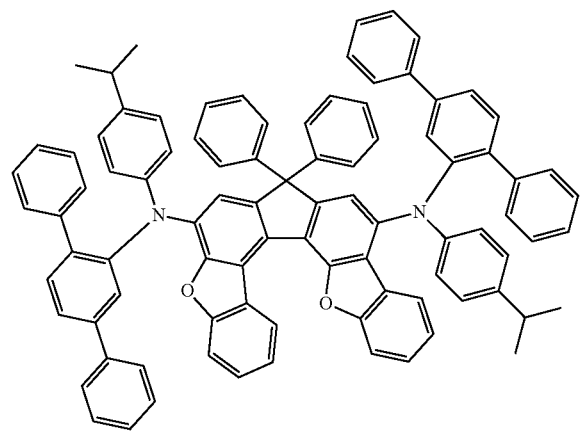
<4>
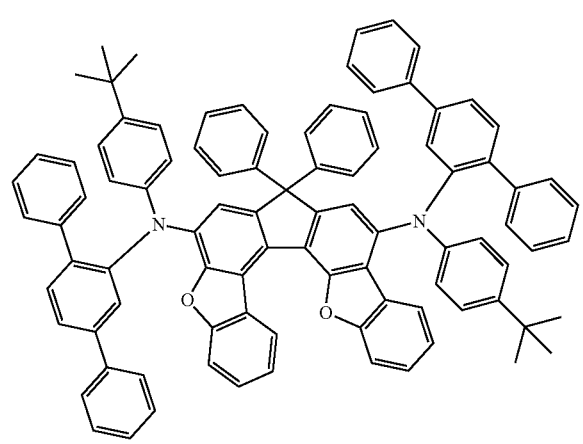
<7>
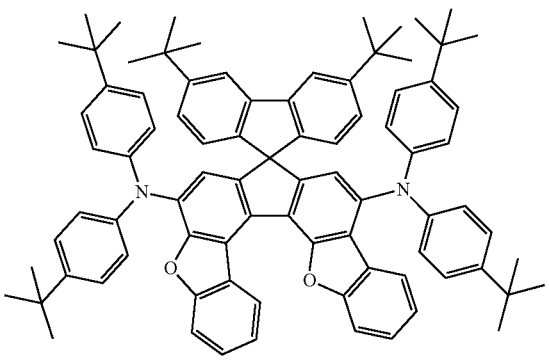
<8>
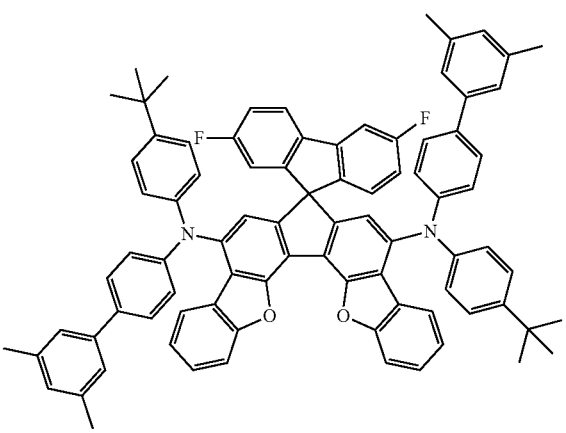
<9>
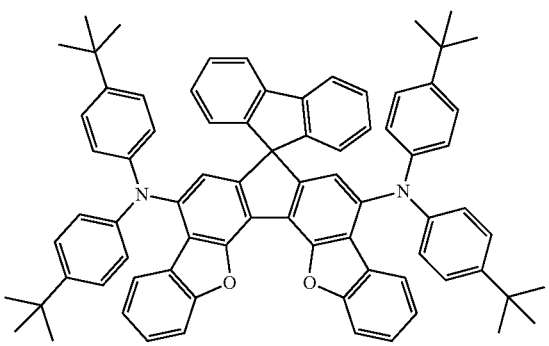
<5>
<6>
<10>
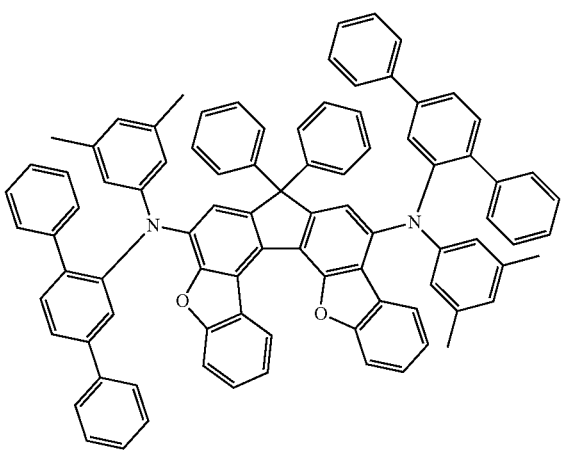

<11>
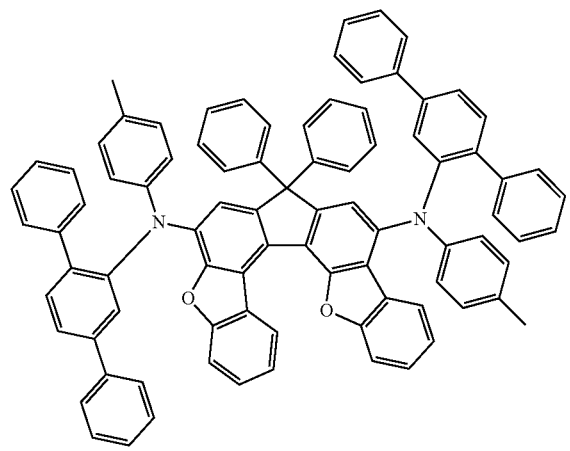
<12>
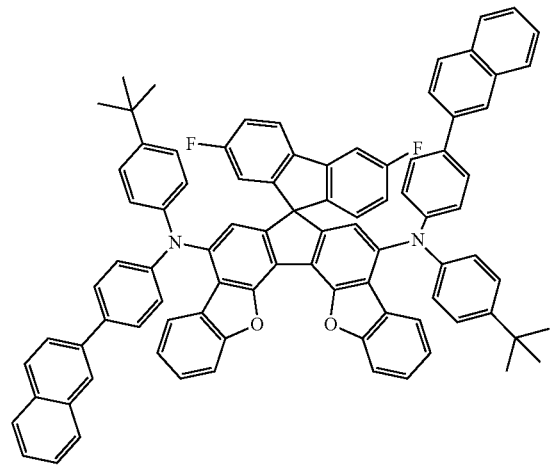
<13>
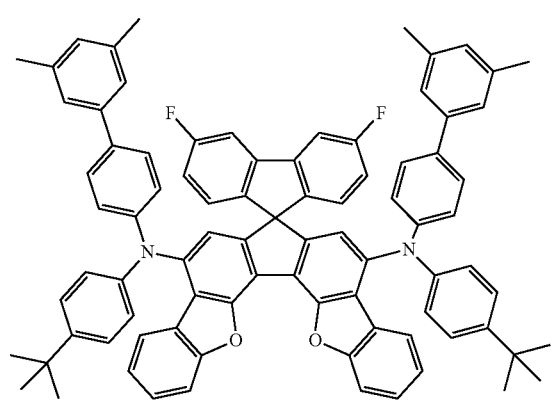
<14>
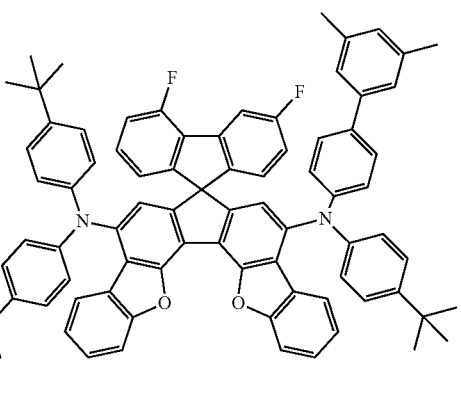
<15>
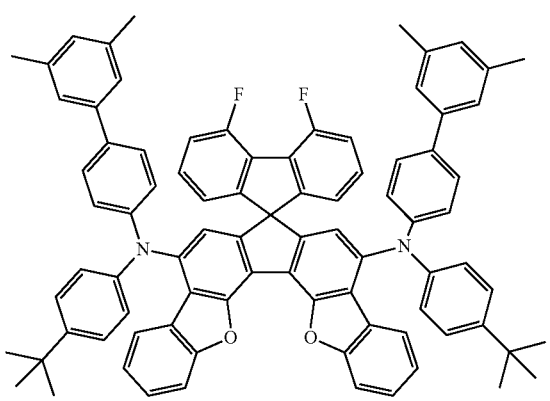
<16>
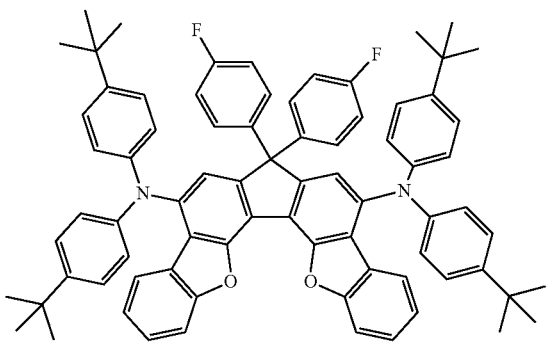
<17>
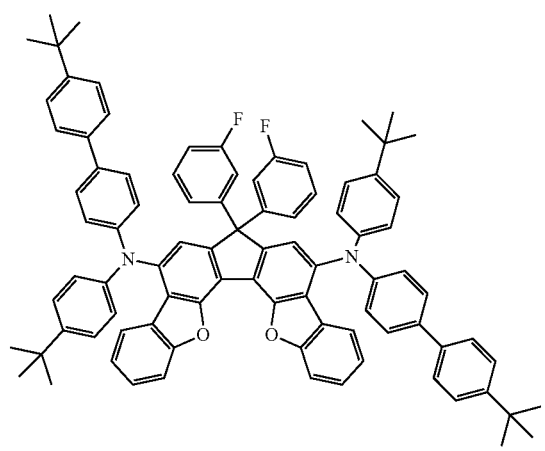

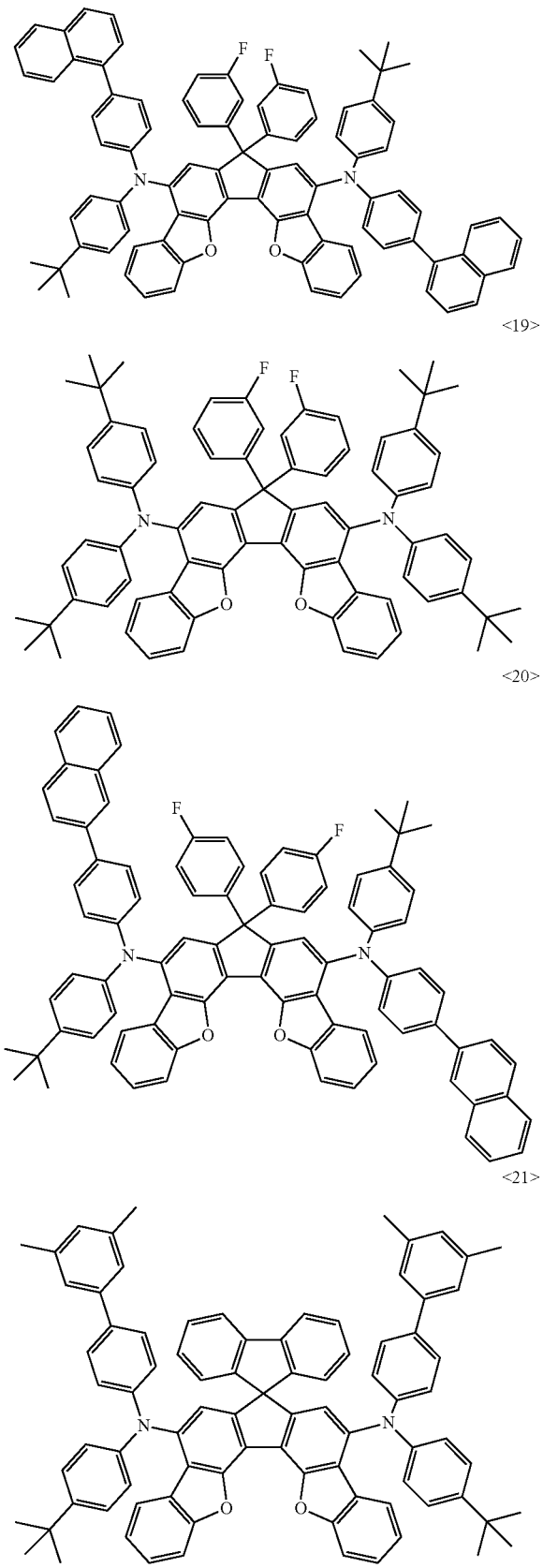

In accordance with an aspect thereof, the present disclosure addresses an organic light-emitting diode, comprising a first electrode; a second electrode facing the first electrode; an organic layer intercalated between the first electrode and the second electrode, wherein the organic layer serves as an emissive layer comprising as an organic luminescent compound at least one of amine compounds represented by Chemical Formula A and emits light with a color coordinate CIEy on a chromaticity diagram of 0.1 or less.

As used herein, the expression "(the organic layer) . . . comprising as an organic luminescent compound at least one of amine compounds" is construed to mean that the organic layer may one or two or more different compounds that fall within the scope of the present disclosure.

In some embodiments of the present disclosure, the emissive layer may comprise a host and a dopant, and the organic luminescent compound of the present disclosure serves as the dopant. Together with a dopant, a host material may be employed in the emissive layer. When the emissive layer comprises a host and a dopant, a content of the dopant may range from about 0.01 to 20 parts by weight based on 100 parts by weight of the host, but is not limited thereto.

In the emissive layer comprising a host and a dopant, when the amine compound represented by [Chemical Formula A] has proper substituents in combination with a suitable host, the light emitted from the emissive layer can have a color coordinate CIEy on a chromaticity diagram of 0.1 or less.

Generally, it is difficult for a conventional organic light-emitting diode using a host and a dopant to emit light at a color coordinate CIEy on a chromaticity diagram of 0.1 or less. Even if emitting light at a color coordinate CIEy on a chromaticity diagram of 0.1 or less, conventional organic light-emitting diodes are nowhere near having high efficiency and a long lifetime.

By way of example, when an arylamine-containing pyrene derivative is used as a dopant while an anthracene derivative serves as a host, the emissive layer is highly unlikely to emit light at a color coordinate CIEy on a chromaticity diagram of 0.1 or less, and exhibits low lifetime and poor efficiency.

In contrast, the organic light-emitting diode employing the amine compound represented by Chemical Formula A as a dopant in an emissive layer in accordance with the present disclosure can readily emit light at a color coordingate CIEy on a chromaticity diagram of 0.1 or less, and has advantage over conventional organic light-emitting diodes in term of efficiency and lifetime.

In some embodiments of the present disclosure, the organic light-emitting diode may emit light at a color coordingate CIEy on a chromaticity diagram of 0.095 or less, particularly at a color coordingate CIEy on a chromaticity diagram of 0.090 or less, more particularly at a color coordingate CIEy on a chromaticity diagram of 0.085 or less, even more particularly at a color coordingate CIEy on a chromaticity diagram of 0.080 or less, far even more particularly at a color coordingate CIEy on a chromaticity diagram of 0.075 or less, and most particularly at a color coordingate CIEy on a chromaticity diagram of 0.070 or less.

In the organic light-emitting diode according to an embodiment of the present disclosure, the host may be an anthracen derivative represented by the following Chemical Formula B.

[Chemical Formula B]

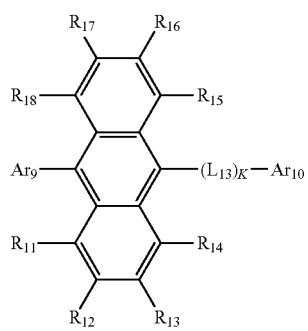

wherein, $R_{11}$ to $R_{13}$ may be the same or different, and are the same as above defined for $R_1$ to $R_9$;

$Ar_9$, and $Ar_{10}$ may be the same or different and may each be independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms;

$L_{13}$ represents a direct bond, or is a substituted or unsubstituted arylene of 6 to 20 carbon atoms or a substituted or unsubstituted heteroarylene of 2 to 20 carbon atoms, k is an integer of 1 to 3, with a proviso that when k is 2 or greater, the corresponding linkers $L_{13}$ may be the same or different.

In a particular embodiment, the substituent $Ar_9$ of Chemical Formula B may be represented by the following Chemical Formula C-1:

[Chemical Formula C-1]

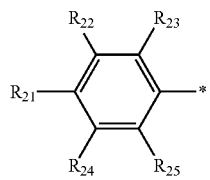

wherein, $R_{21}$ to $R_{25}$ may be the same or different and are each the same as above defined for $R_1$ to $R_9$; an adjacent two of them may be bonded to each other to form a saturated or unsaturated ring.

In a particular embodiment, $L_{13}$ represents a direct bond or a substituted or unsubstituted arylene of 6 to 20 carbon atoms, and k is an integer of 1 to 2, with a proviso that when k is 2, the corresponding linkers $L_{13}$ may be the same or different.

According to some embodiments of the present disclosure, the anthracene derivative may be one selected from among compounds represented by the following [Chemical Formula 22] to [Chemical Formula 60]:

<22>

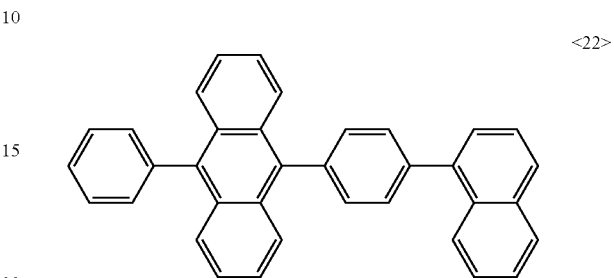

<23>

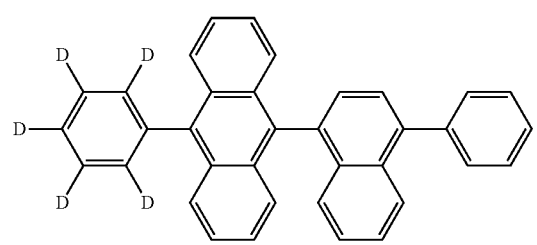

<24>

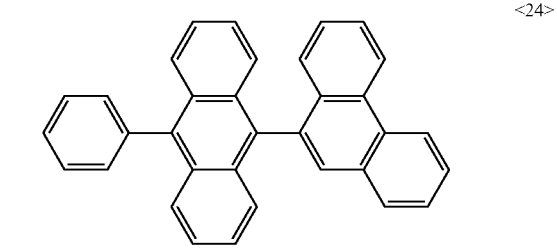

<25>

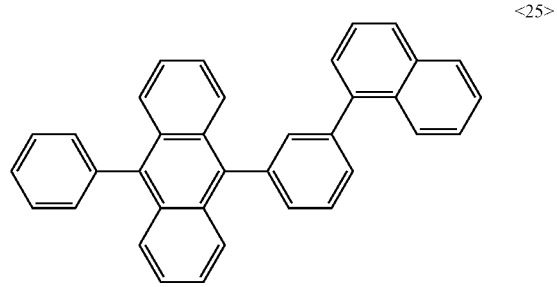

<26>

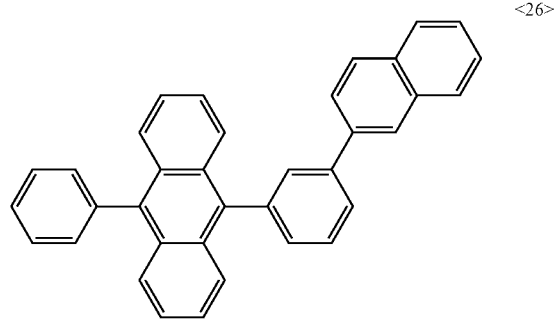

<27>
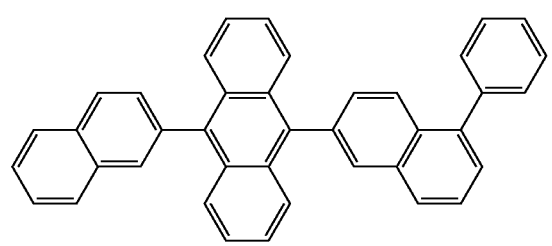
<28>
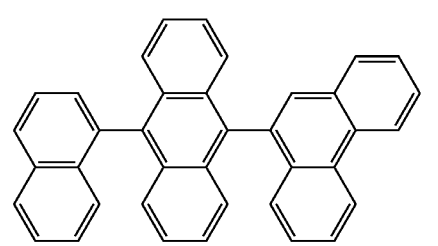
<29>
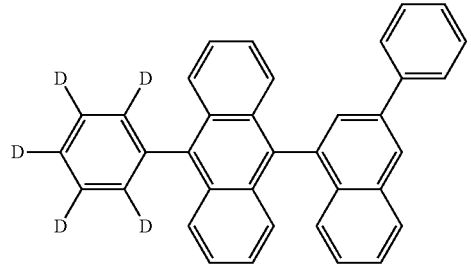
<30>
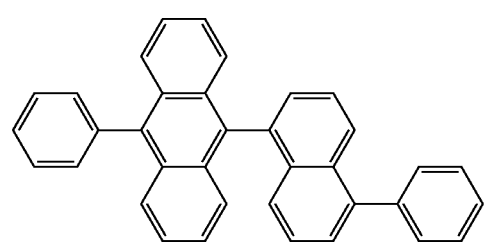
<31>
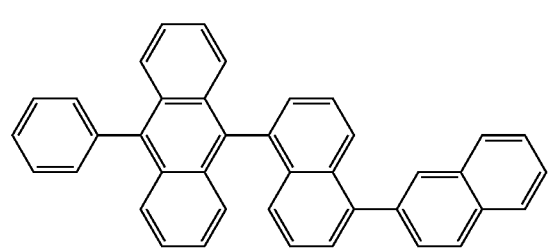
<32>
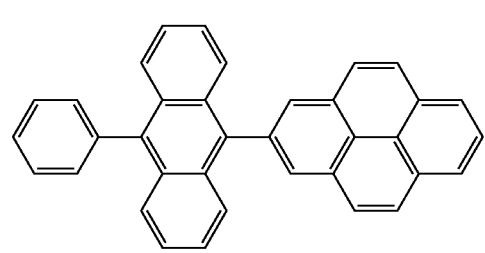
<33>
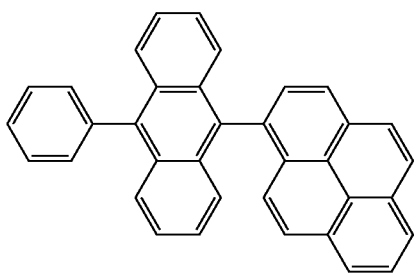
<34>
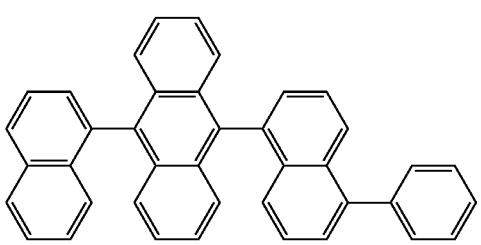
<35>
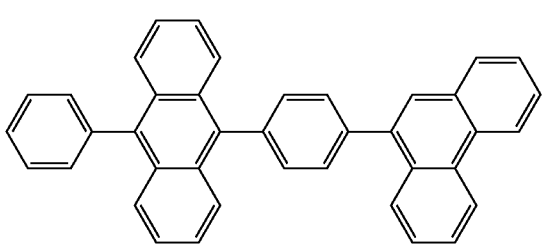
<36>
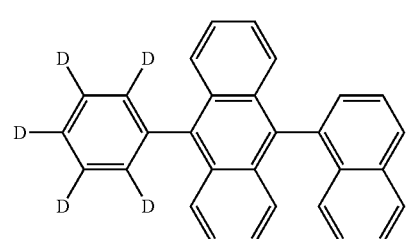
<37>
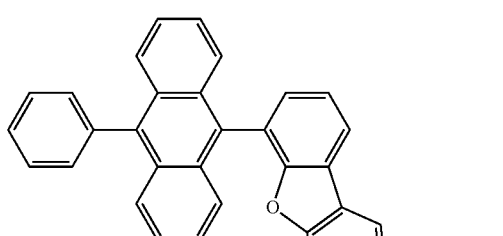

<38>
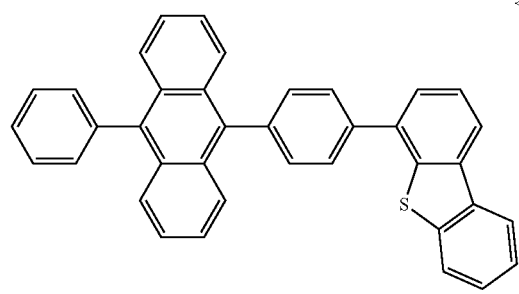
<43>
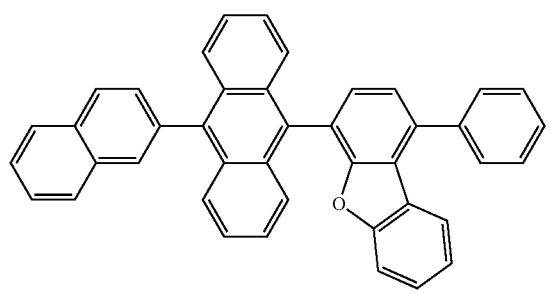
<39>
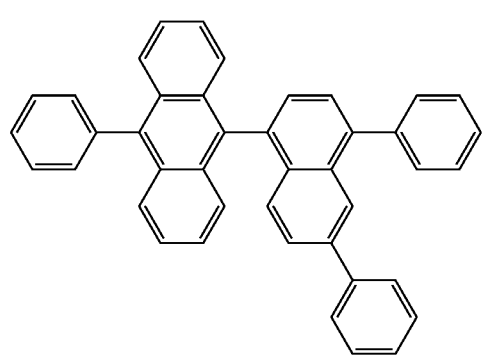
<44>
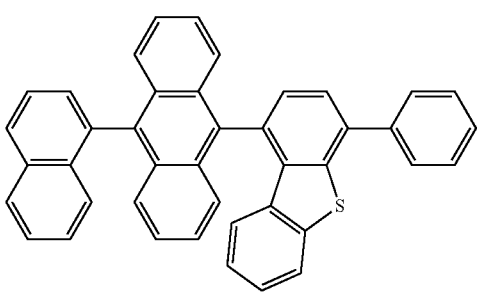
<40>
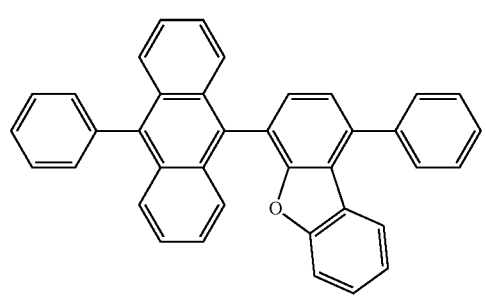
<45>
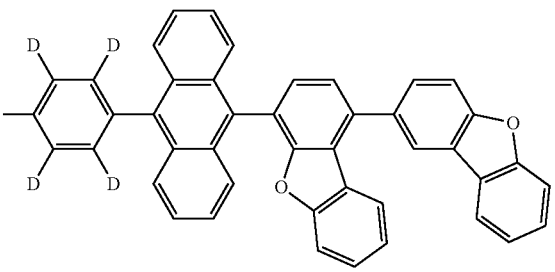
<41>
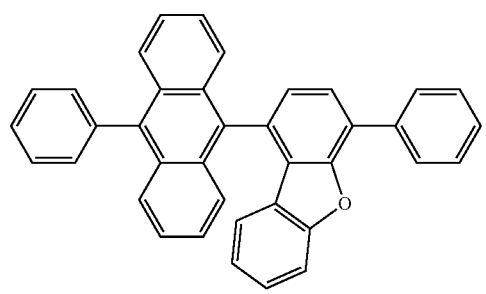
<46>
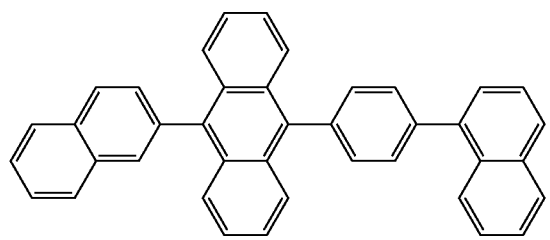
<42>
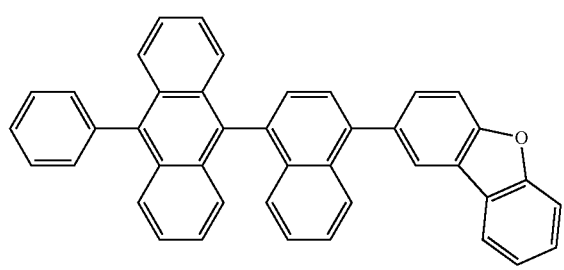
<47>

<48>
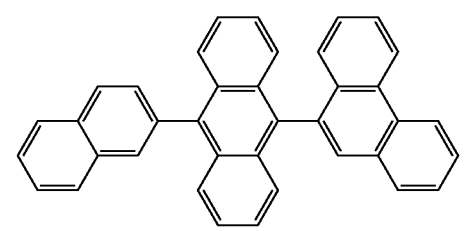
<49>
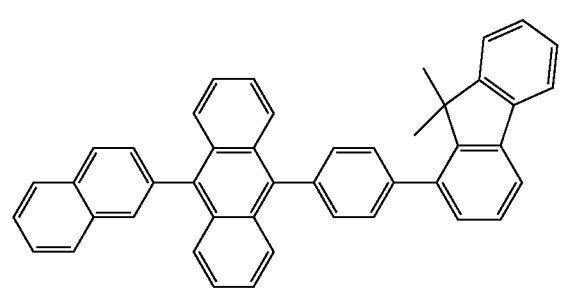
<50>
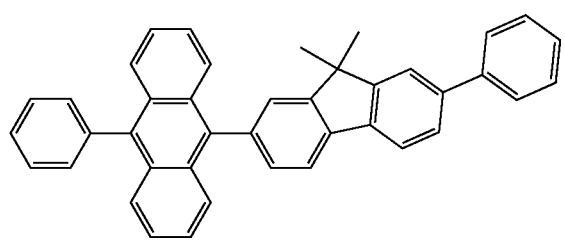
<51>
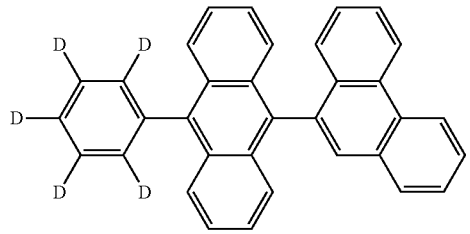
<52>
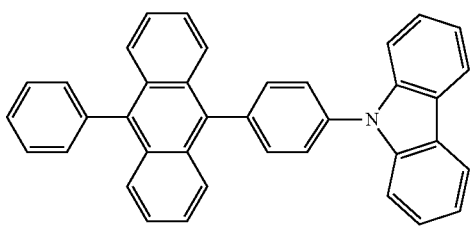
<53>
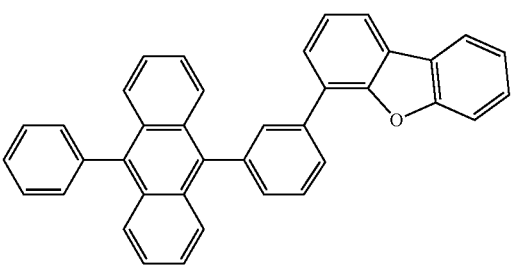
<54>
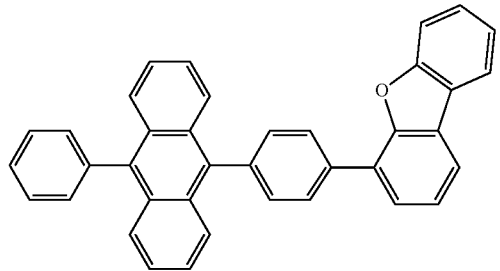
<55>
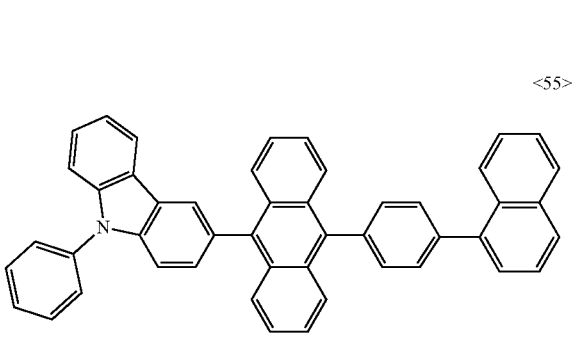
<56>
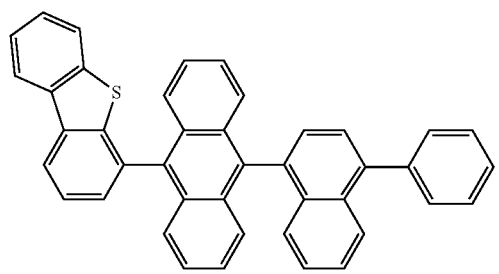
<57>
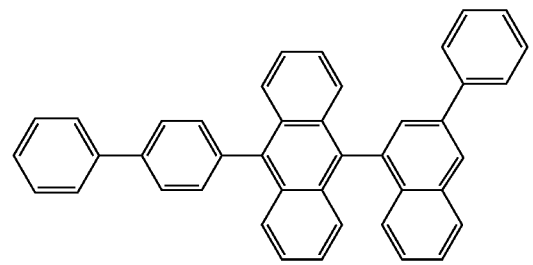
<58>
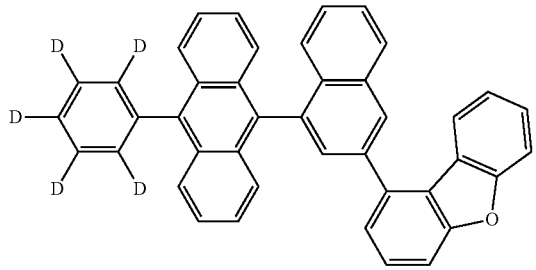

<59>

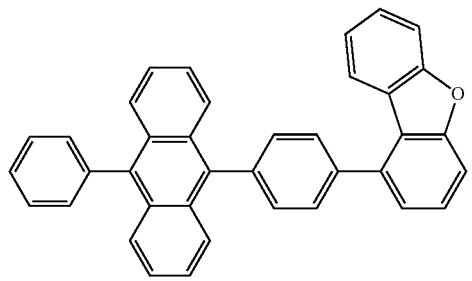

<60>

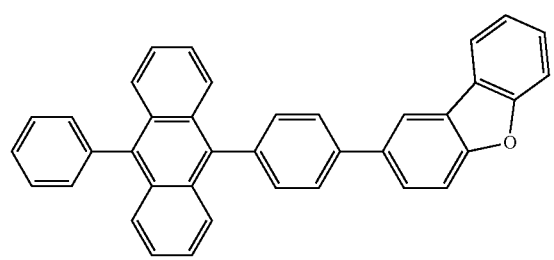

TAZ

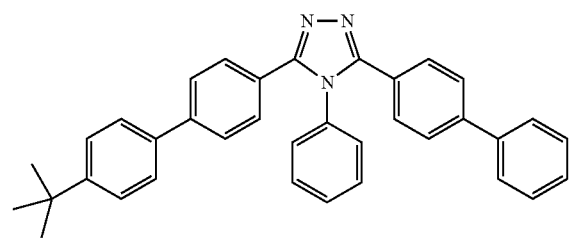

BAlq

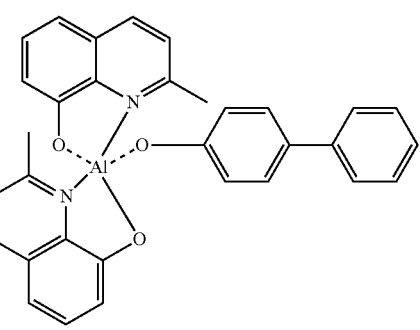

<Compound 201>

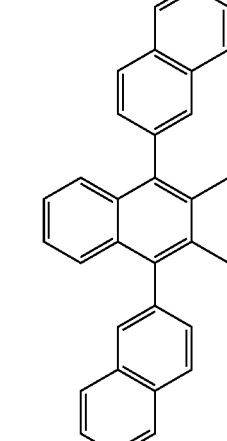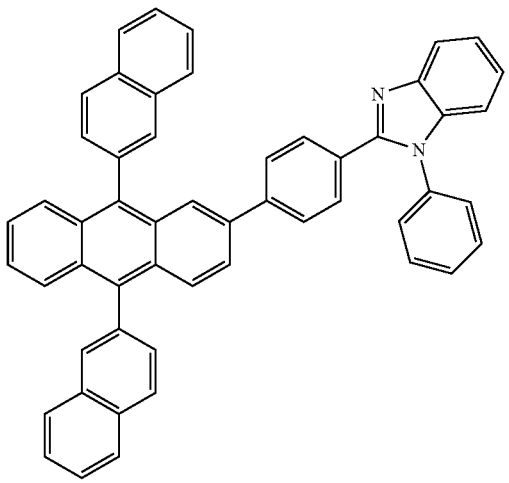

<Compound 202>

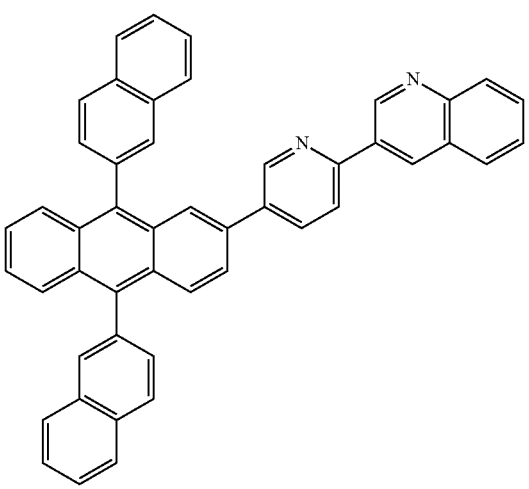

Also, the emissive layer may further comprise various dopant materials in addition to the dopant and the host.

On the other hand, the organic light-emitting diode of the present disclosure may comprise two or more emissive layers composed of at least one layer employing a phosphorescent material and at least one layer employing the compound represented by Chemical Formula A.

The organic light-emitting diode having the structure illustrated above in accordance with the present disclosure can find applications in the illumination system field as well as the display field. For example, the deep blue light of the organic light-emitting diode of the present disclosure can be utilized by applying the organic light-emitting diode to a flat or flexible light device emitting monochrome or white light.

In a particular embodiment, the phosphorescent material used in the emissive layer may be a source of redish yellow or yellow light with a mean wavelength of 550~620 nm, and particularly 570~600 nm.

According to some particular embodiments of the present disclosure, the organic light-emitting diode may comprise at least one of a hole injection layer, a hole transport layer, a functional layer capable of both hole injection and hole transport, an electron transport layer, and an electron injection layer in addition to the emissive layer.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum (Alq3), TAZ, Balq, beryllium bis(benzoquinolin-10-olate) (Bebq2), ADN, Compound 201, Compound 202, BCP, and oxadiazole derivatives such as PBD, BMD, BND, etc., but are not limited thereto.

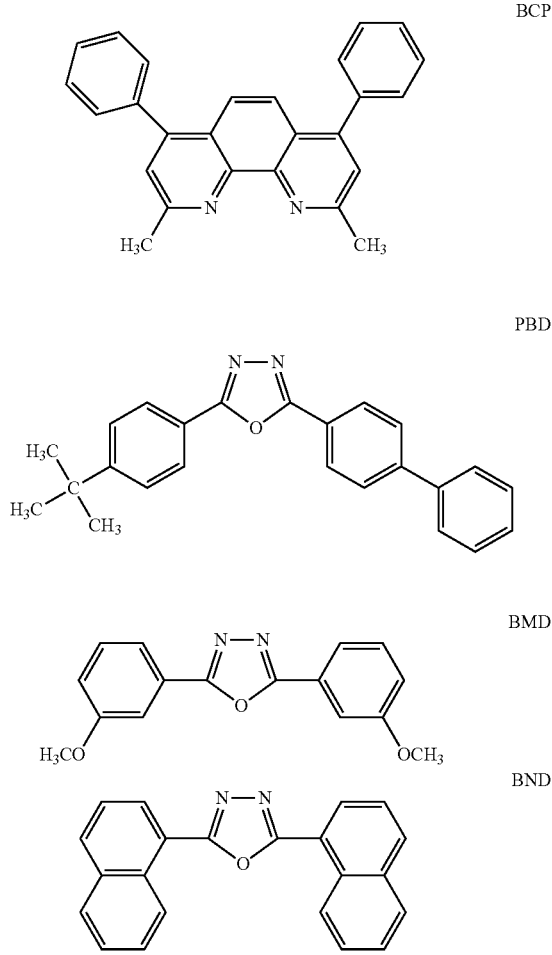

BCP

PBD

BMD

BND

Below, a description will be given of the organic light-emitting diode of the present disclosure, with reference to FIG. 1.

FIG. 1 is a schematic cross-sectional view of the structure of an organic light-emitting diode according to some embodiments of the present disclosure. The organic light-emitting diode comprises an anode 20, a hole transport layer 40, an organic emissive layer 50, electron transport layer 60, and cathode 80, and optionally a hole injection layer 30 and an electron injection layer 70. In addition, one or two intermediate layers may be further formed in the organic light-emitting diode, or a hole barrier layer or an electron barrier layer may also be employed.

Reference is made to FIG. 1 with regard to the fabrication of the organic light-emitting diode of the present disclosure. First, a substrate 10 is coated with an anode electrode material to form an anode 20. So long as it is used in a typical organic EL device, any substrate may be taken as the substrate 10. Preferable is an organic substrate or transparent plastic substrate that exhibits excellent transparency, surface smoothness, and handleability. As the anode electrode material, indium tin oxide (ITO), indium zinc oxide (IZO), tin oxide ($SnO_2$), or zinc oxide (ZnO) may be used.

A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imparted to a hole injection layer material that is typically used in the art. For example, mention may be made of 2-TNATA [4,4',4"-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine].

So long as it is typically used in the art, any material for the hole transport layer may be selected without particular limitations. Examples include, but are not limited to, N,N'-bis(3-methylphenyl)-N,N'-diphenyl-[1,1-biphenyl]-4,4'-diamine (TPD) or N,N'-di(naphthalen-1-yl)-N,N'-diphenyl-benzidine (a-NPD).

Then, an organic emissive layer 50 is deposited on the hole transport layer 40, optionally followed by the formation of a hole barrier layer (not shown) on the organic emissive layer 50 by deposition in a vacuum or by spin coating. When holes traverse the organic emissive layer and are introduced into the cathode, the diode becomes poor in efficiency and lifetime. Formed of a material with a low HOMO (Highest Occupied Molecular Orbital) level, the hole barrier layer serves to prevent the introduction of holes into the cathode. Any material that has a higher ionization potential than the light emitting compound, as well as being able to carry electrons may be used for the hole barrier layer without limitations. Representative among the hole barrier materials are BAlq, BCP, and TPBI.

Using a vacuum deposition method or a spin coating method, an electron transport layer 60 may be deposited on the hole barrier layer, and then overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminu-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the emissive layer particularly ranges in thickness from 50 to 2,000 Å.

Further, one or more layers selected from among a hole injection layer, a hole transport layer, an electron barrier layer, an emissive layer, a hole barrier layer, an electron transport layer, and an electron injection layer may be deposited using a single molecule deposition process or a solution process. Here, the deposition process refers to a process by which a material is vaporized in a vacuum or at a low pressure and deposited to form a layer, and the solution process means a method in which a material is dissolved in a solvent and applied for the formation of a thin film by means of inkjet printing, roll-to-roll coating, screen printing, spray coating, dip coating, spin coating, etc.

Also, the organic light-emitting device of the present disclosure may be applied to a device selected from among flat display devices; flexible display devices; monochrome or white flat illumination devices; and monochrome or white flexible illumination devices.

A better understanding of the present invention may be obtained through the following examples which are set forth to illustrate, but are not to be construed as the limit of the present invention.

EXAMPLES

Synthesis Example 1: Synthesis of Chemical Formula 1

Synthesis Example 1-(1): Synthesis of Intermediate 1-a

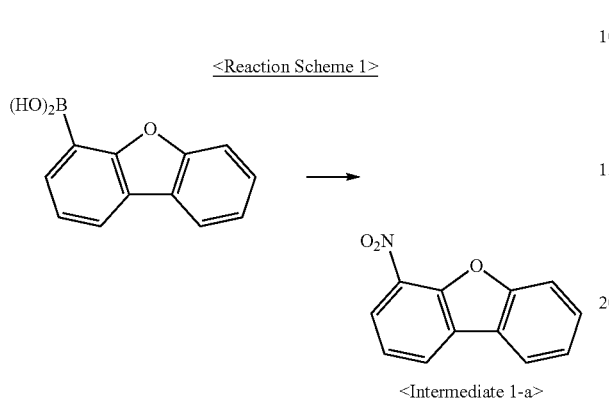

<Intermediate 1-a>

In a 1-L round-bottom flask reactor, dibenzofuran-4-bronic acid (85.0 g, 0.401 mol), bismuth (III) nitrate pentahydrate (99.2 g, 0.200 mol), and toluene (400 ml) were reacted at 70° C. for hrs under a nitrogen atmosphere while stirring. After completion of the reaction, the reaction mixture was cooled to room temperature and washed with toluene. Filtration afforded <Intermediate 1-a> as a solid (61.5 g, 72%).

Synthesis Example 1-(2): Synthesis of Intermediate 1-b

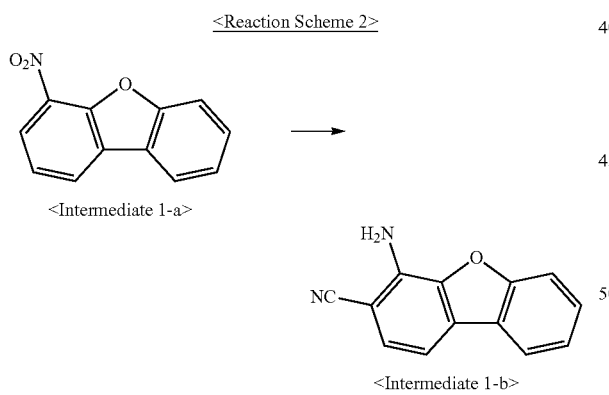

<Intermediate 1-b>

In a 2-L round-bottom flask reactor, ethylcyanoacetate (202.9 g, 1.794 mol), and dimethylformamide (500 ml) were added with potassium hydroxide (67.10 g, 1.196 mol), potassium cyanide (38.95 g, 0.598 mol), and dimethylformamide (200 ml), followed by stirring at room temperature. To this reaction solution, <Intermediate 1-a> (127.5 g, 0.737 mol) was slowly added while stirring at 50° C. for 72 hrs. After completion of the reaction, an aqueous sodium hydroxide solution (25%, 200 ml) was added, and stirred for 3 hrs under reflux. Subsequently, the reaction mixture was cooled to room temperature, followed by extraction with ether acetate and water. The organic layer was separated and concentrated. Purification by column chromatography afforded <Intermediate 1-b> (20.0 g, 16%).

Synthesis Example 1-(3): Synthesis of Intermediate 1-c

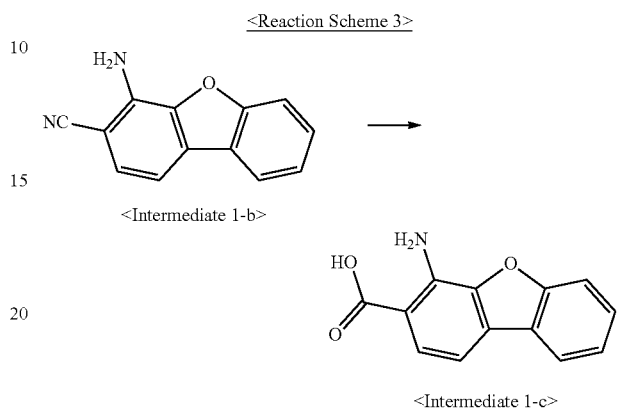

<Intermediate 1-c>

In a 2-L round-bottom flask reactor, <Intermediate 1-b> (20.0 g, 0.096 mol), ethanol (600 ml), and an aqueous solution (170 ml) of potassium hydroxide solution (142.26 g, 2.53 mol) were stirred for 12 hrs under reflux. After completion of the reaction, the reaction mixture was cooled to room temperature, and acidified with 6 N HCl (400 ml). Then, the reaction mixture was stirred for 20 min, and filtered. The filtrate was washed with ethanol to afford <Intermediate 1-c> as a solid (17.0 g, 88.5%).

Synthesis Example 1-(4)

Synthesis of Intermediate 1-d

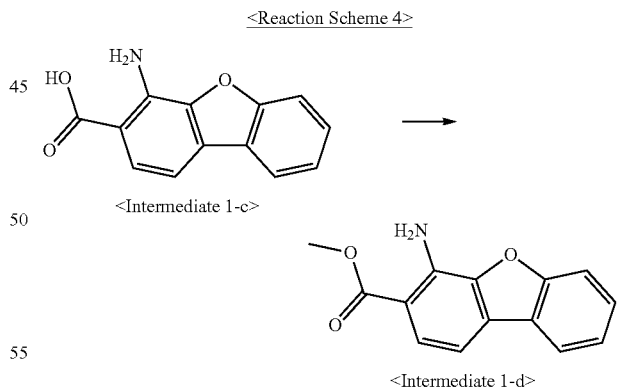

<Intermediate 1-d>

In a 2-L round-bottom flask reactor, <Intermediate 1-c> (17.0 g, 0.07 mol) and sulfuric acid (15 ml) were stirring together for 72 hrs under reflux. After completion of the reaction, the reaction mixture was cooled to room temperature and extracted with ethylacetate and water. The organic layer was separated, and washed with an aqueous sodium hydrogen carbonate solution. An excess of methanol was added during vacuum concentration, followed by filtration to afford <Intermediate 1-d> as a solid (14.0 g, 77.6%).

Synthesis Example 1-(5): Synthesis of Intermediate 1-e

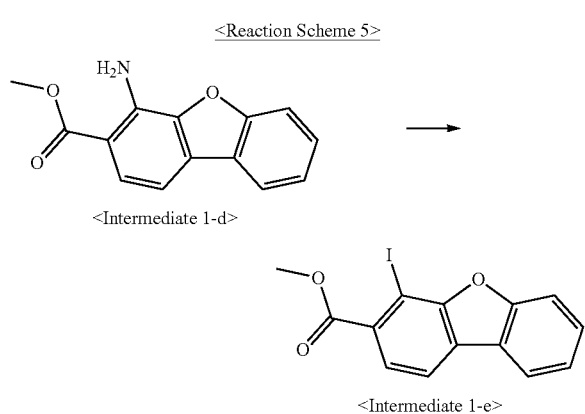

In a 500-mL round-bottom flask reaction, <Intermediate 1-d> (14.0 g, 0.058 mol), HCl (20 ml), and water (100 ml) were stirred together for 1 hr at 0° C. At the same temperature, an aqueous solution (50 ml) of sodium nitrite (7.4 g, 0.116 mol) was dropwise added to the reaction mixture and then stirred for 1 hr. An aqueous solution (100 ml) of potassium iodide (30.0 g, 0.180 mol) was dropwise added with care not to increase the temperature of the reaction solution above 5° C. Stirring was continued for 5 hrs at room temperature, and after completion of the reaction, the reaction mixture was washed with an aqueous sodium thiosulfate solution, and extracted with ethylacetate and water. The organic layer was separated and concentrated in a vacuum. Purification through column chromatography gave <Intermediate 1-e> (9.1 g, 48%).

Synthesis Example 1-(6): Synthesis of Intermediate 1-f

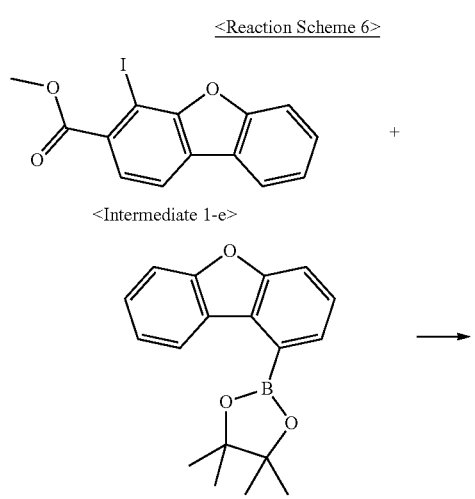

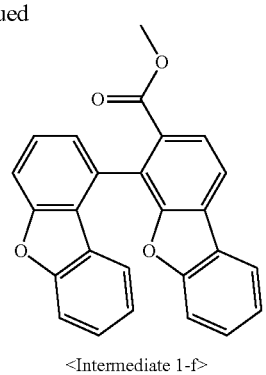

In a 250-mL round-bottom flask reactor, <Intermediate 1-e>(9.3 g, 25 mmol), 1-dibenzofuranborate (8.3 g, 28 mmol), tetrakis(triphenylphosphine)palladium (0.6 g, 0.05 mmol), and potassium carbonate (6.7 g, 50 mmol) were placed, and then toluene (50 ml), tetrahydrofuran (50 mL), and water (20 mL) were added. The temperature of the reactor was elevated to 80° C. before stirring for 10 hrs. After completion of the reaction, the temperature was cooled to room temperature, and extraction was conducted with ethylacetate. The organic layer thus formed was concentrated in a vacuum and purified by column chromatography to afford <Intermediate 1-f> (5.3 g, 52.3%).

Synthesis Example 1-(7)

Synthesis of Intermediate 1-g

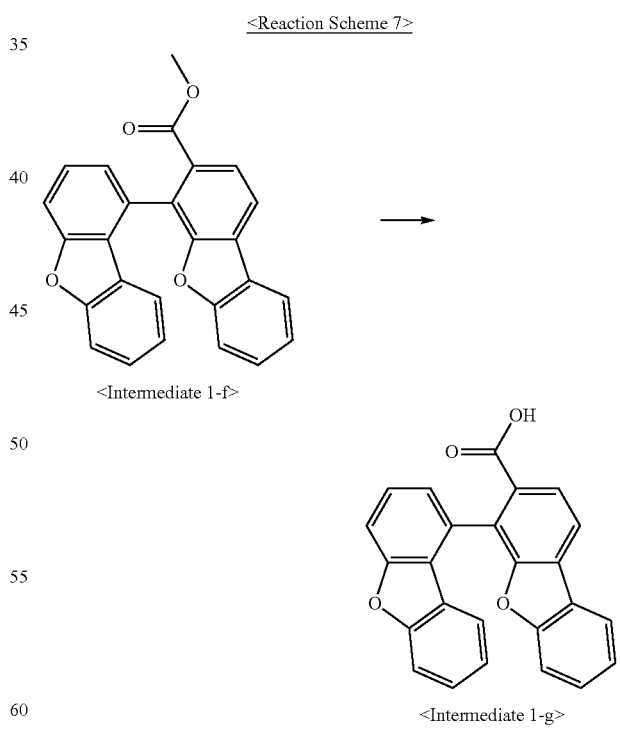

In a 100-mL round-bottom flask reactor, <Intermediate 1-f>(5.3 g, 15 mmol), sodium hydroxide (0.7 g, 17 mmol), and ethanol (50 ml) were stirred for 48 under reflux. After completion of the reaction was confirmed by thin layer chromatography, the reaction mixture was cooled to room temperature. To the cooled solution, drops of 2-N HCl were added over 30 min while stirring. Recrystallization in dichloromethane and normal hexane afforded <Intermediate 1-g> as a solid (4.5 g, 88.0%).

Synthesis Example 1-(8): Synthesis of Intermediate 1-h

Intermediate 1-h was synthesized according to the following Reaction Scheme 8:

<Reaction Scheme 8>

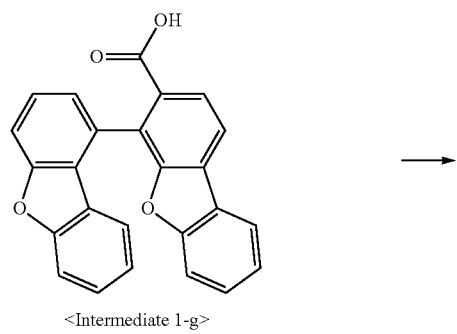

<Intermediate 1-g>

<Intermediate 1-h>

In a 100-ml round-bottom flask reactor, <Intermediate 1-g>(4.5 g, 12 mmol) was reacted with methane sulfonic acid (30 ml) at 80° C. for 3 hrs while stirring. After completion of the reaction was configured by thin layer chromatography, drops of the reaction mixture were slowly added to ice water (50 ml), and then stirred for 30 min. Filtration and washing with water and methanol gave <Intermediate 1-h> as a solid (3.8 g, 88.8%).

Synthesis Example 1-(9): Synthesis of Intermediate 1-i

<Reaction Scheme 9>

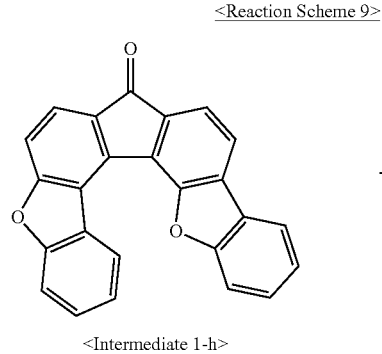

<Intermediate 1-h>

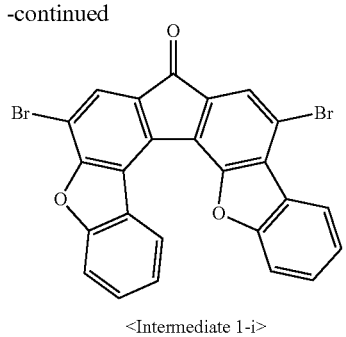

<Intermediate 1-i>

In a 100-mL, round-bottom flask reactor, <Intermediate 1-h>(3.8 g, 11 mmol> was stirred together with dichloromethane (40 ml) at room temperature, and then a dilution of bromine (1.1 ml, 22 mmol) in dichloromethane (10 ml) was dropwise added, followed by stirring at room temperature for 8 hrs. After completion of the reaction, acetone (20 ml) was added to the reactor and stirred. The precipitate thus formed was filtered, and washed with acetone. Recrystallization in monochlorobenzene gave <Intermediate 1-i> as a solid (3.0, 55%).

Synthesis Example 1-(10)

Synthesis of Intermediate 1-j

<Reaction Scheme 10>

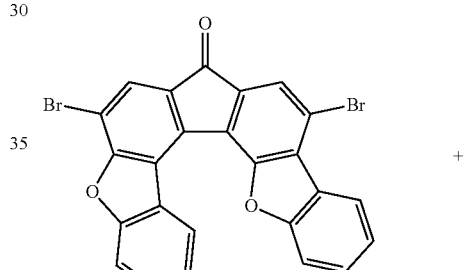

<Intermediate 1-i>

<Intermediate 1-j>

In a 100-ml round-bottom flask reactor, a mixture of 2-bromobiphenyl (2.1 g, 0.009 mol) and tetrahydrofuran (30 ml) was cooled to −78° C. under a nitrogen atmosphere. At the same temperature, n-butyl lithium (4.8 ml, 0.008 mol) was dropwise added to the mixture, and stirred for 2 hrs. Then, <Intermediate 1-i> (3.0 g, 0.006 mol) was added little by little at room temperature while stirring. When the reaction mixture started a color change, the reaction was monitored by thin layer chromatography. After the reaction was stopped with H₂O (10 ml), extraction was conducted with ethylacetate and water. The organic layer was separated, concentrated in a vacuum, and recrystallized with acetonitrile to afford <Intermediate 1-j> as a solid (2.5 g, 64%).

Synthesis Example 1-(11): Synthesis of Intermediate 1-k

<Reaction Scheme 11>

Synthesis Example 1-(12): Synthesis of Chemical Formula 1

<Reaction Scheme 12>

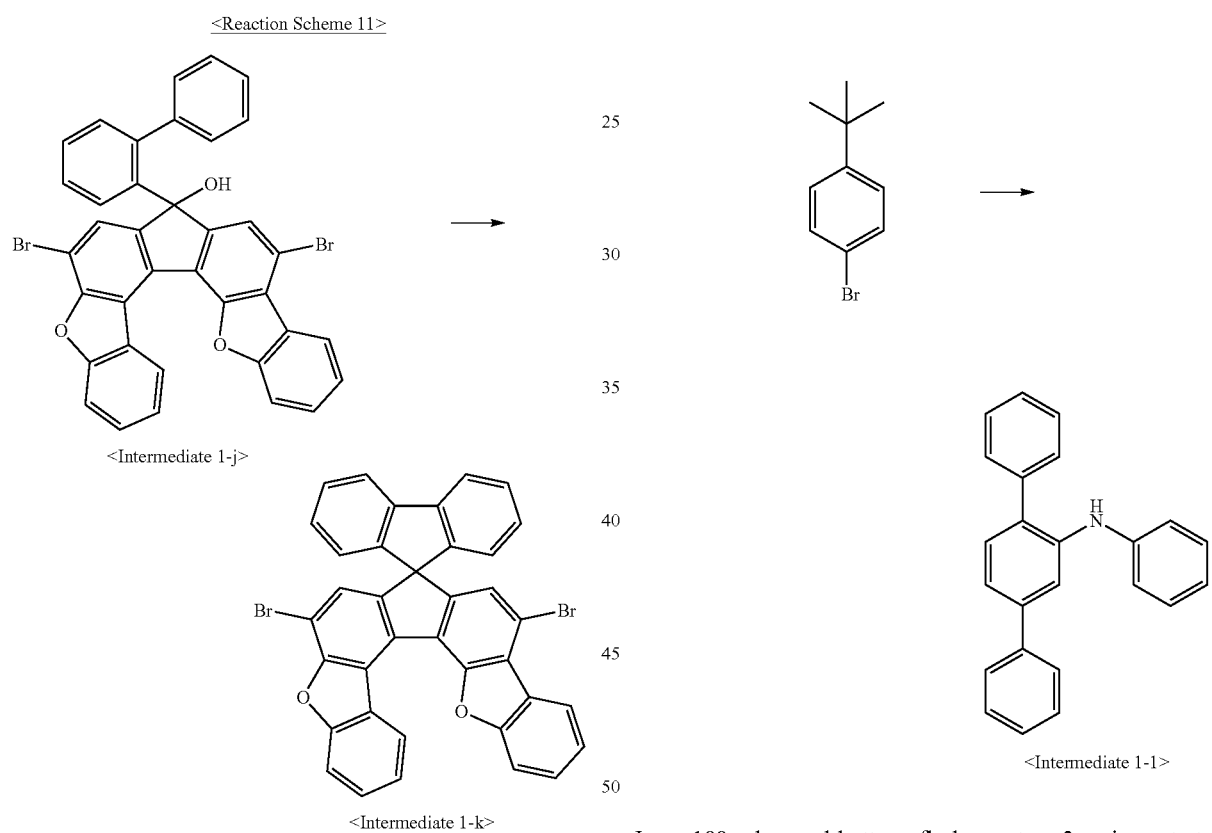

In a 100-ml round-bottom flask reactor, a mixture of <Intermediate 1-j> (2.5 g, 0.04 mol), acetic acid (25 ml), and sulfuric acid (0.5 ml) was stirred for 5 hrs under reflux. When a precipitate was formed, the completion of the reaction was monitored by thin layer chromatography. The reaction mixture was then cooled to room temperature, and filtered. The filtrate was washed with H₂O and methanol, and dissolved in monochlorobenzene. Following silica gel chromatography, the fraction was concentrated and cooled to room temperature to give <Intermediate 1-k> (2.2 g, 90%).

In a 100-ml round-bottom flask reactor, 2-amino-p-tert-phenyl (0.7 g, 0.003 mol), 1-bromo 4-tert-butylbenzene (1.7 g, 0.008 mol), palladium (II) acetate (0.04 g, 0.2 mmol), sodium tert-butoxide (1.6 g, 0.016 mol), and tri-tert-butyl phosphine (0.04 g, 0.2 mmol) were stirred together with 30 ml of toluene for 2 hrs under reflux. After completion of the reaction, the reaction mixture was cooled to room temperature, and extracted with dichloromethane and water. The organic layer thus formed was separated, dried over magnesium sulfate, and concentrated in a vacuum. The concentrate was purified by column chromatography and recrystallized in dichloromethane and acetone to afford <Intermediate 1-l> as a solid (0.95 g, 63%).

Synthesis Example 1-(13): Synthesis of Chemical Formula 1

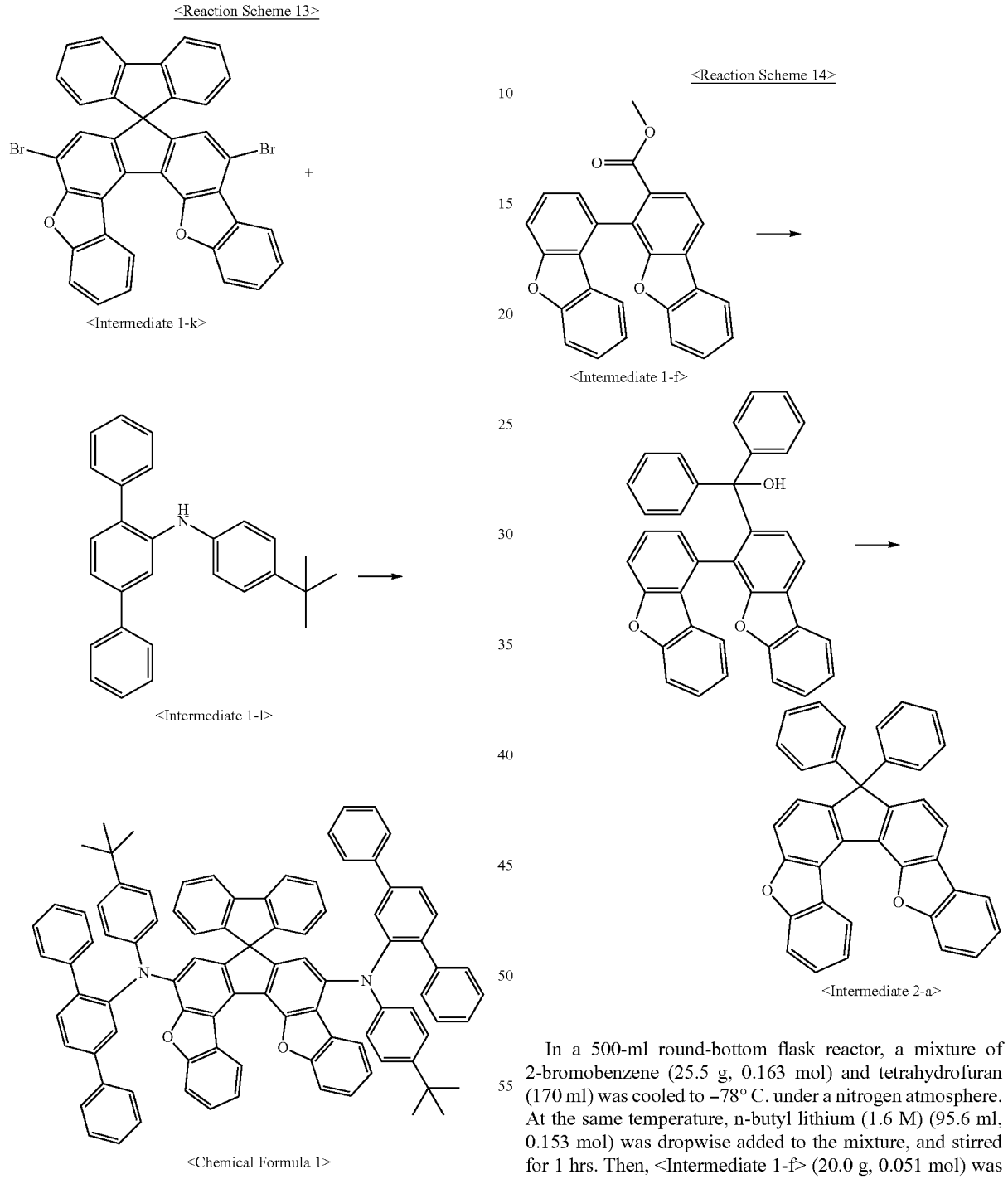

With the exception that <intermediate 1-l> and <intermediate 1-k> was used instead of 2-amino-p-tert-phenyl and 1-bromo 4-tert-butylbenzene, the same procedure as in Synthesis Example 1-(12) was carried out to afford <Chemical Formula 1> (13.1 g, 50%).

MS (MALDI-TOF): m/z 1247.55 [M⁺]

Synthesis Example 2: Synthesis of Chemical Formula 4

Synthesis Example 2-(1): Synthesis of Intermediate 2-a

In a 500-ml round-bottom flask reactor, a mixture of 2-bromobenzene (25.5 g, 0.163 mol) and tetrahydrofuran (170 ml) was cooled to −78° C. under a nitrogen atmosphere. At the same temperature, n-butyl lithium (1.6 M) (95.6 ml, 0.153 mol) was dropwise added to the mixture, and stirred for 1 hrs. Then, <Intermediate 1-f> (20.0 g, 0.051 mol) was added and stirred at room temperature for 3 hrs. After completion of the reaction, water (50 ml) was added to the reaction mixture that was then stirred for 30 min. The reaction mixture was extracted with ethylacetate and water, and the organic layer was separated and concentrated in a vacuum. The concentrate was mixed with acetic acid (200 ml) and HCl (1 ml) and stirred at 80° C. When the reaction was completed, the reaction mixture was cooled to room temperature, and filtered. The filtrate was washed with methanol to afford <Intermediate 2-a> as a solid (20.0 g, 78%).

Synthesis Example 2-(2): Synthesis of Intermediate 2-b

<Reaction Scheme 15>

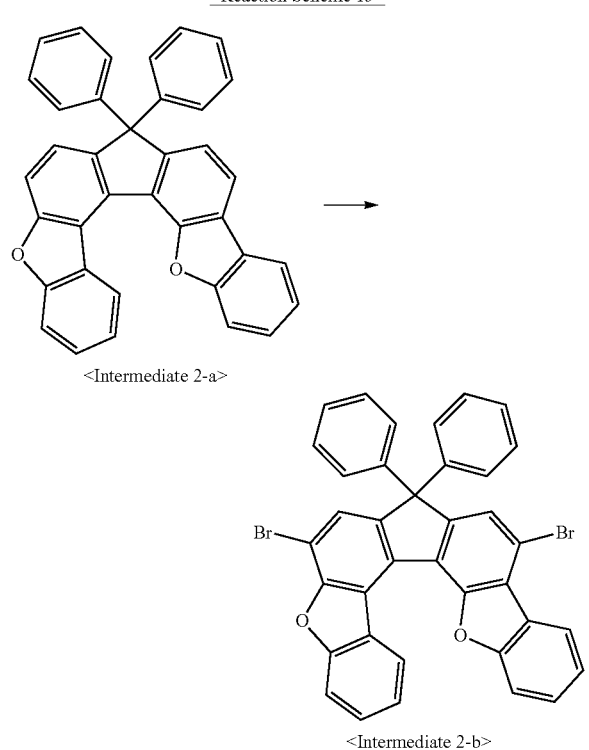

<Intermediate 2-a>

<Intermediate 2-b>

With the exception that <Intermediate 2-a> was used instead of <Intermediate 1-h>, the same procedure as in Synthesis Example 1-(9) was carried out to afford <Intermediate 2-b> (5.7 g, 63%).

Synthesis Example 2-(3)

Synthesis of Chemical Formula 4

<Reaction Scheme 16>

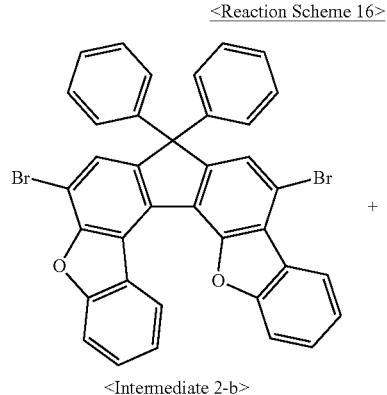

<Intermediate 2-b>

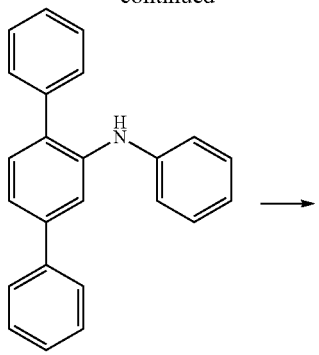

<Intermediate 1-1>

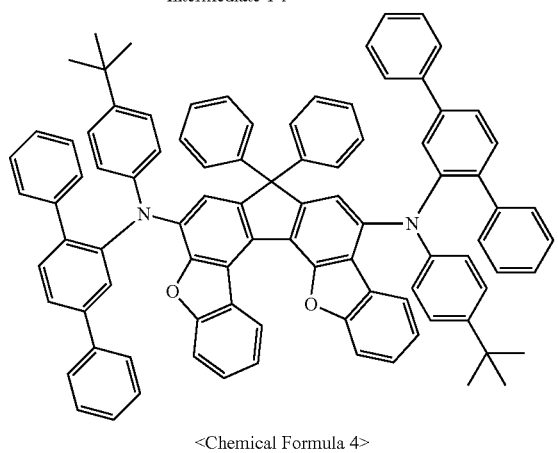

<Chemical Formula 4>

With the exception that <intermediate 1-1> and <Intermediate 2-b> were used instead of 2-amino-p-tert-phenyl and 1-bromo 4-tert-butylbenzene, respectively, the same procedure as in Synthesis Example 1-(12) was carried out to afford <Chemical Formula 4> (3.2 g, 49%).

MS (MALDI-TOF): m/z 1249.56 [M$^+$]

Synthesis Example 3: Synthesis of Chemical Formula 5

<Reaction Scheme 17>

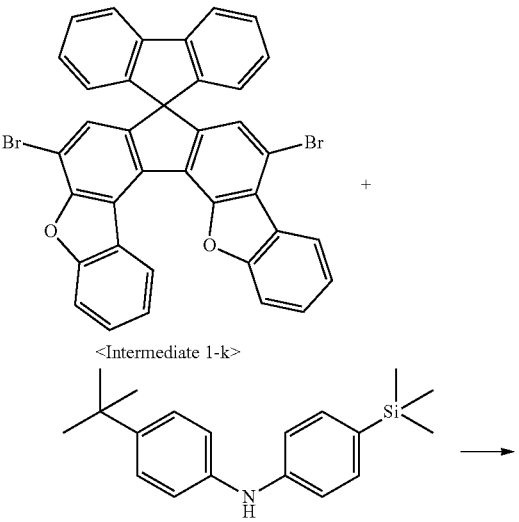

<Intermediate 1-k>

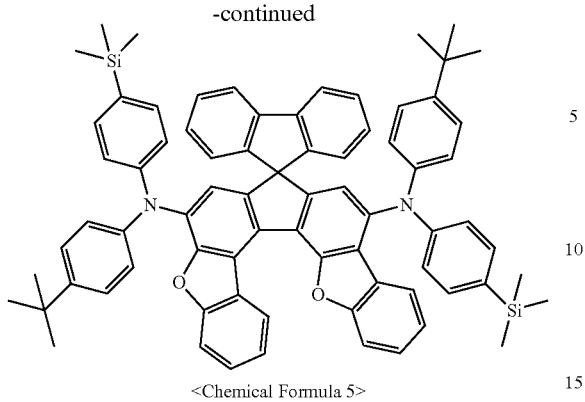

<Chemical Formula 5>

With the exception that 4-(tert-butyl)-N-(4-(trimethylsilyl)phenyl)amine and <Intermediate 1-k> were used instead of 2-amino-p-tert-phenyl and 1-bromo 4-tert-butylbenzene, respectively, the same procedure as in Synthesis Example 1-(12) was carried out to afford <Chemical Formula 5>(2.3 g, 43%).

MS (MALDI-TOF): m/z 1088.5 [M$^+$]

Synthesis Example 4: Synthesis of Chemical Formula 7

Synthesis Example 4-(1): Synthesis of Intermediate 4-a

<Reaction Scheme 18>

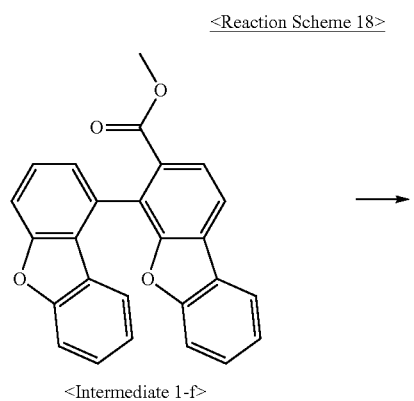

<Intermediate 1-f>

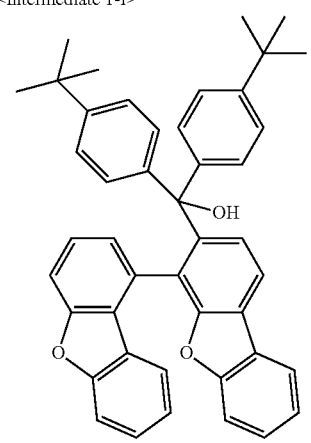

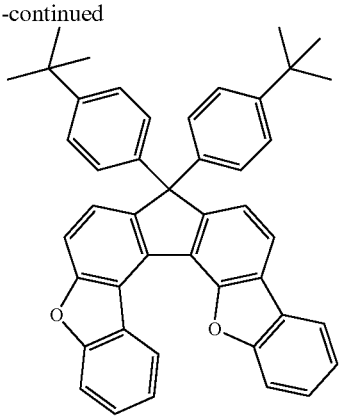

<Intermediate 4-a>

With the exception that 1-bromo-4-(tert-butyl)benzene was used instead of bromobenzene, the same procedure as in Synthesis Example 2-(1) was carried out to afford Intermediate 4-a> (12.2 g, 47%).

Synthesis Example 4-(2)

Synthesis of intermediate 4-b

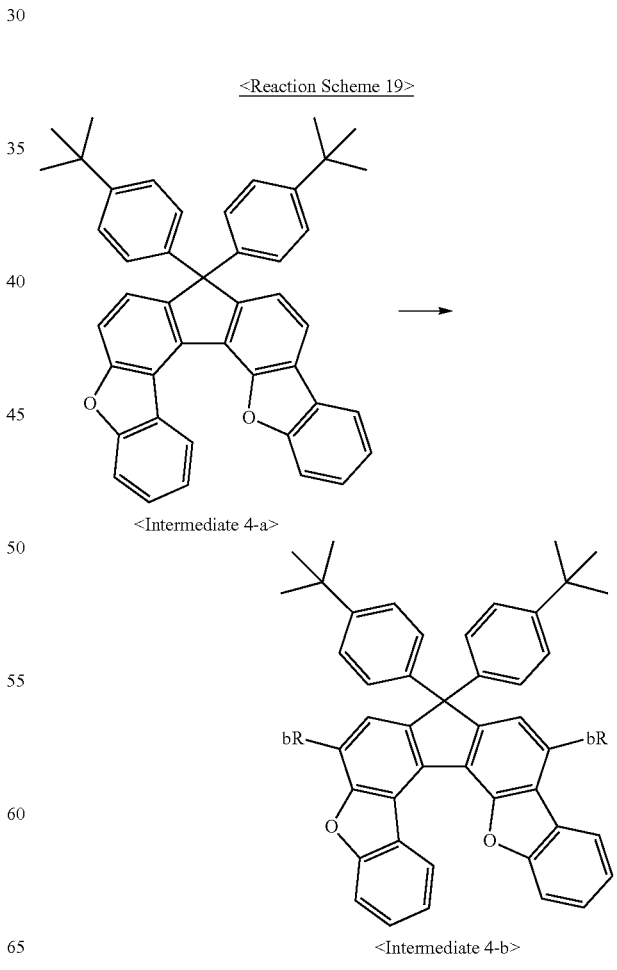

<Reaction Scheme 19>

<Intermediate 4-a>

<Intermediate 4-b>

With the exception that Intermediate 4-a> was used instead of <Intermediate 1-h>, the same procedure as in Synthesis Example 1-(9) was carried out to afford <Intermediate 4-b> (10.0 g, 65%).

Synthesis Example 4-(3): Synthesis of Chemical Formula 7

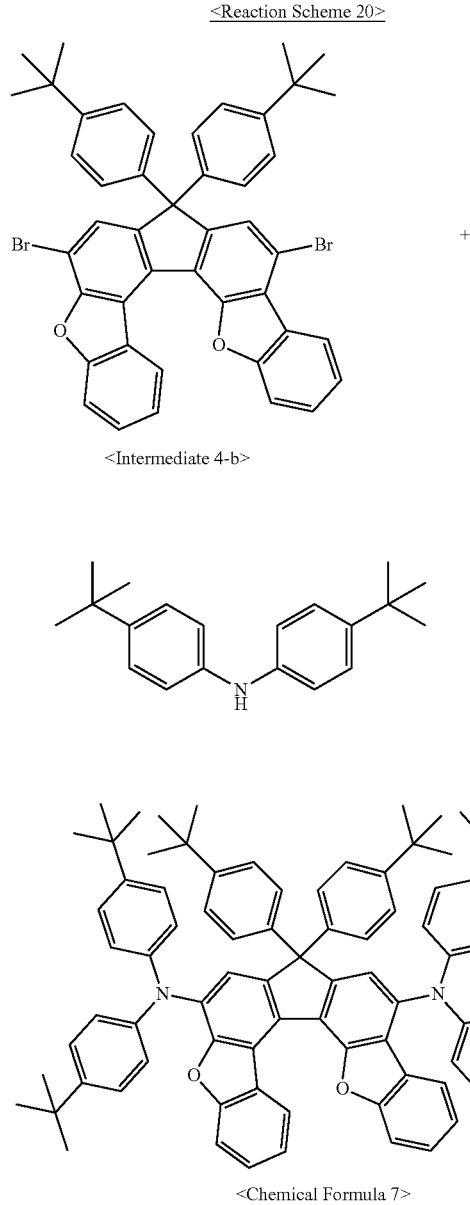

<Reaction Scheme 20>

<Intermediate 4-b>

<Chemical Formula 7>

With the exception that bis(4-tert-butylpheny)amine and <Intermediate 4-b> were used instead of 2-amino-p-tert-phenyl and 1-bromo 4-tert-butylbenzene, respectively, the same procedure as in Synthesis Example 1-(12) was carried out to afford <Chemical Formula 7> (8.2 g, 54%).

MS (MALDI-TOF): m/z 1170.6 [M+]

Synthesis Example 5: Synthesis of Chemical Formula 9

Synthesis Example 5-(1)

Synthesis of Intermediate 5-a

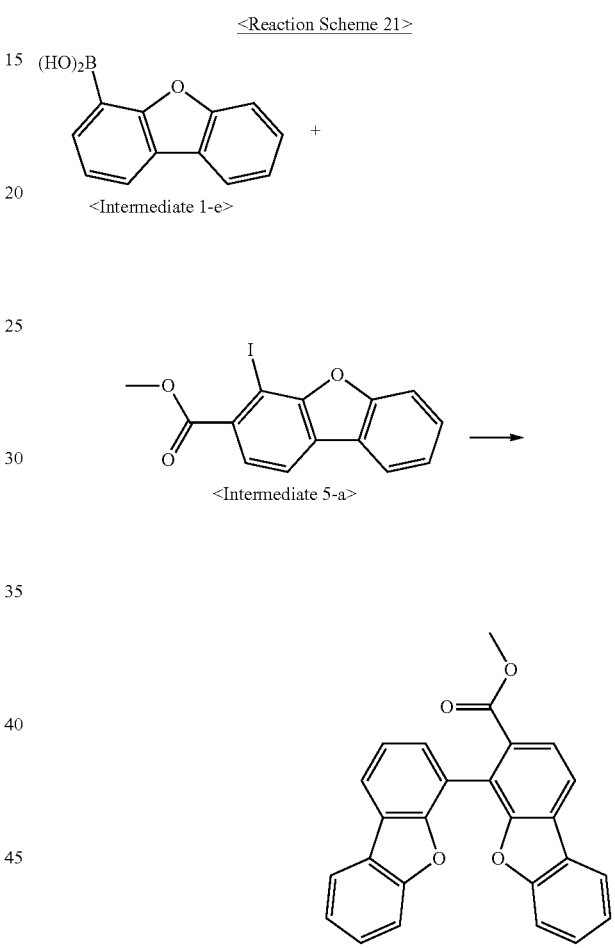

<Reaction Scheme 21>

<Intermediate 1-e>

<Intermediate 5-a>

In a 250-mL round-bottom flask reactor, <Intermediate 1-e> (9.3 g, 25 mmol), 4-dibenzofuran bronic acid (8.3 g, 28 mmol), tetrakis(triphenylphosphine)palladium (0.6 g, 0.05 mmol), and potassium carbonate (6.7 g, 50 mmol) were placed, followed by the addition of toluene (100 mL), tetrahydrofuran (100 mL), and water (20 mL). The temperature of the reactor was elevated to 80° C. before stirring for 10 hrs. After completion of the reaction, the temperature was cooled to room temperature, and extraction was conducted with ethylacetate. The organic layer thus formed was concentrated in a vacuum and purified by column chromatography to afford <Intermediate 5-a> (5.3 g, 52.3%).

Synthesis Example 5-(2)

Synthesis of Intermediate 5-b

<Reaction Scheme 22>

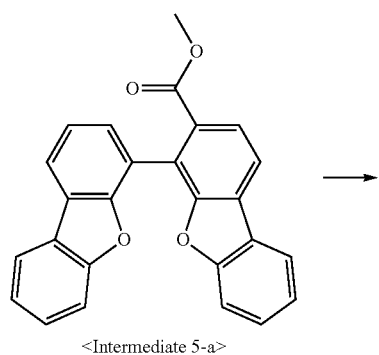

<Intermediate 5-a>

→

<Intermediate 5-b>

With the exception of using <Intermediate 5-a> instead of <Intermediate 1-f>, the same procedure as in Synthesis Example 1-(7) was carried out to afford <Intermediate 5-b> (4.5 g, 88.0%).

Synthesis Example 5-(3): Synthesis of Intermediate 5-c

Intermediate 1-h was synthesized according to the following Reaction Scheme 8:

<Reaction Scheme 23>

<Intermediate 5-b>

→

<Intermediate 5-c>

With the exception of using <Intermediate 5-b> instead of <Intermediate 1-g>, the same procedure as in Synthesis Example 1-(8) was carried out to afford <Intermediate 5-c> (3.8 g, 88.0%).

Synthesis Example 5-(4): Synthesis of Intermediate 5-d

<Reaction Scheme 24>

<Intermediate 5-c>

→

<Intermediate 5-d>

With the exception of using <Intermediate 5-c> instead of <Intermediate 1-h>, the same procedure as in Synthesis Example 1-(9) was carried out to afford <Intermediate 5-d> (3.0 g, 55%).

Synthesis Example 5-(5)

Synthesis of Intermediate 5-e

<Reaction Scheme 25>

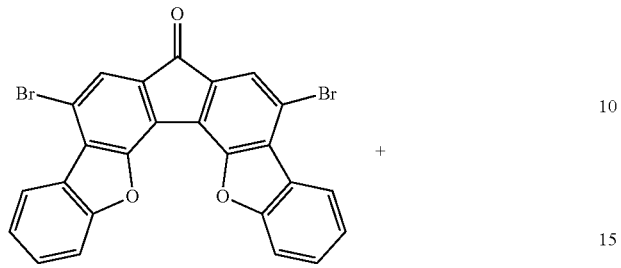

<Intermediate 5-d>

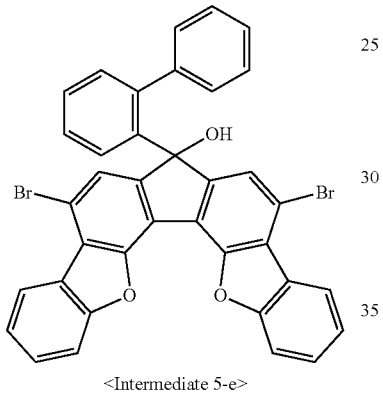

<Intermediate 5-e>

With the exception of using <Intermediate 5-d> instead of <Intermediate 1-i>, the same procedure as in Synthesis Example 1-(10) was carried out to afford <Intermediate 5-e> (2.5 g, 64%).

Synthesis Example 5-(6)

Synthesis of Intermediate 5-f

<Reaction Scheme 26>

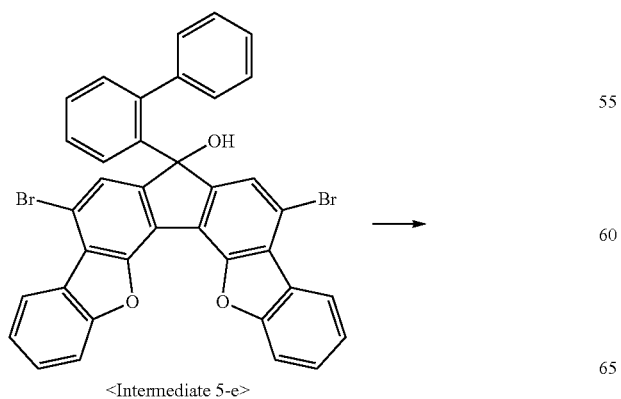

<Intermediate 5-e>

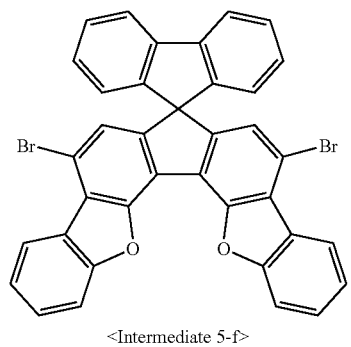

<Intermediate 5-f>

With the exception of using <Intermediate 5-e> instead of <Intermediate 1-j>, the same procedure as in Synthesis Example 1-(11) was carried out to afford <Intermediate 5-f> (2.2 g, 90%).

Synthesis Example 5-(7)

Synthesis of Chemical Formula 9

<Reaction Scheme 27>

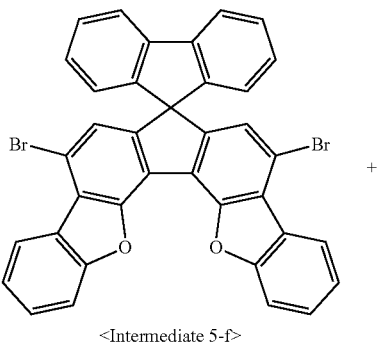

<Intermediate 5-f>

+

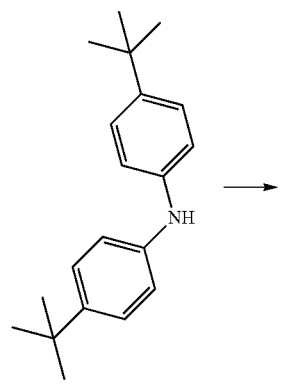

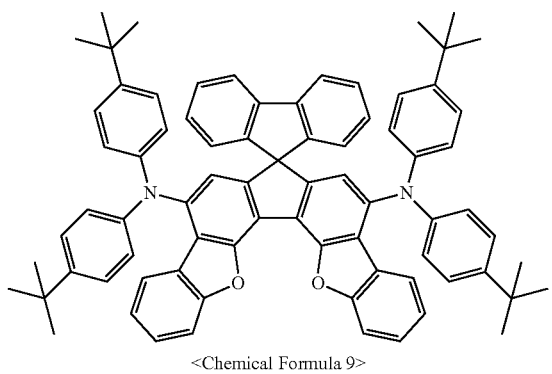

<Chemical Formula 9>

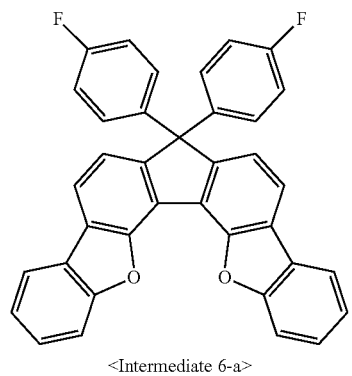

<Intermediate 6-a>

With the exception of using <Intermediate 5-f> and bis(4-tert-butylpheneyl)amine instead of 1-bromo 4-tert-butylbenzene and 2-amino-p-tert-phenyl, respectively, the same procedure as in Synthesis Example 1-(12) was carried out to afford <Chemical Formula 9> (13.1 g, 50%).

MS (MALDI-TOF): m/z 1054.54 [M⁺]

With the exception of using <Intermediate 5-a> and 1-bromo-4-fluorobenzene instead of <Intermediate 1-f> and bromobenzene, respectively, the same procedure as in Synthesis Example 2-(1) was carried out to afford <Intermediate 6-a> (12.2 g, 47%).

Synthesis Example 6: Synthesis of Chemical Formula 16

Synthesis Example 6-(1): Synthesis of Intermediate 6-a

Synthesis Example 6-(2): Synthesis of Intermediate 6-b

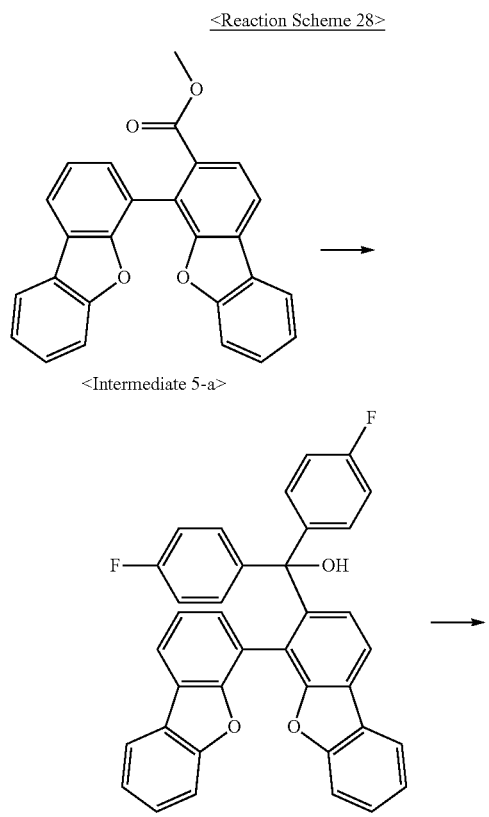

<Reaction Scheme 28>

<Intermediate 5-a>

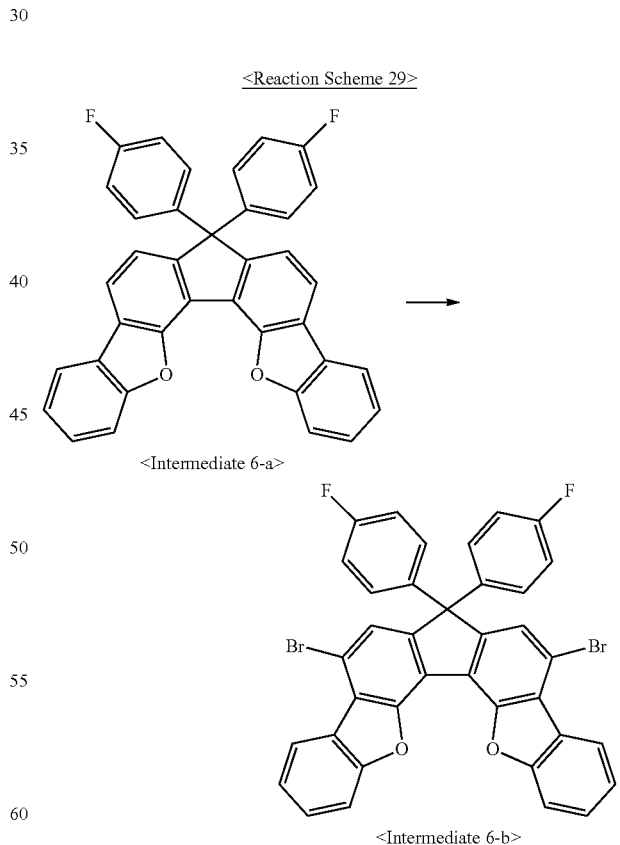

<Reaction Scheme 29>

<Intermediate 6-a>

<Intermediate 6-b>

With the exception of using <Intermediate 6-a> instead of <Intermediate 1-h>, the same procedure as in Synthesis Example 1-(9) was carried out to afford <Intermediate 6-b> (10.0 g, 65%)

Synthesis Example 6-(3): Synthesis of Chemical Formula 16

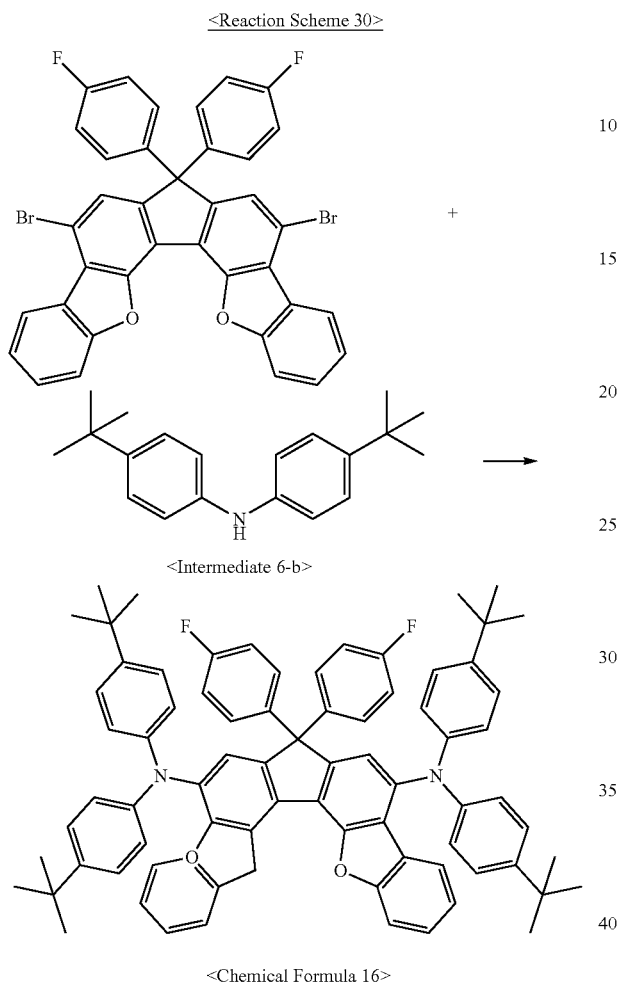

<Reaction Scheme 30>
<Intermediate 6-b>
<Chemical Formula 16>

With the exception of using <Intermediate 6-b> and bis(4-tert-butylpheneyl)amine instead of 1-bromo 4-tert-butylbenzene and 2-amino-p-tert-phenyl, respectively, the same procedure as in Synthesis Example 1-(12) was carried out to afford <Chemical Formula 16> (8.2 g, 54%).

MS (MALDI-TOF): m/z 1092.54 [M⁺]

Examples 1 to 12: Fabrication of Organic Light-Emitting Diode

An ITO glass substrate was patterned to have a luminescence area of 2 mm×2 mm, and cleansed. The ITO glass was mounted in a vacuum chamber that was then set to have a base pressure of $1\times10^{-7}$ torr. On the ITO glass substrate, films were formed of HAT-CN (50 Å) and α-NPD (600 Å) in the order. An emissive layer (200 Å) was formed of a mixture of a host and a dopant (5 wt %) as shown in Table 1, below. Then, a mixture of 1:1 [Chemical Formula E-1]:[Chemical Formula E-2] was deposited to form an electron transport layer 300 Å thick, on which an electron injection layer (10 Å) was formed of [Chemical Formula E-1] and covered with an Al layer (1000 Å) to fabricate an organic light-emitting diode. The organic light-emitting diodes thus obtained were measured at 0.4 mA for luminescence properties.

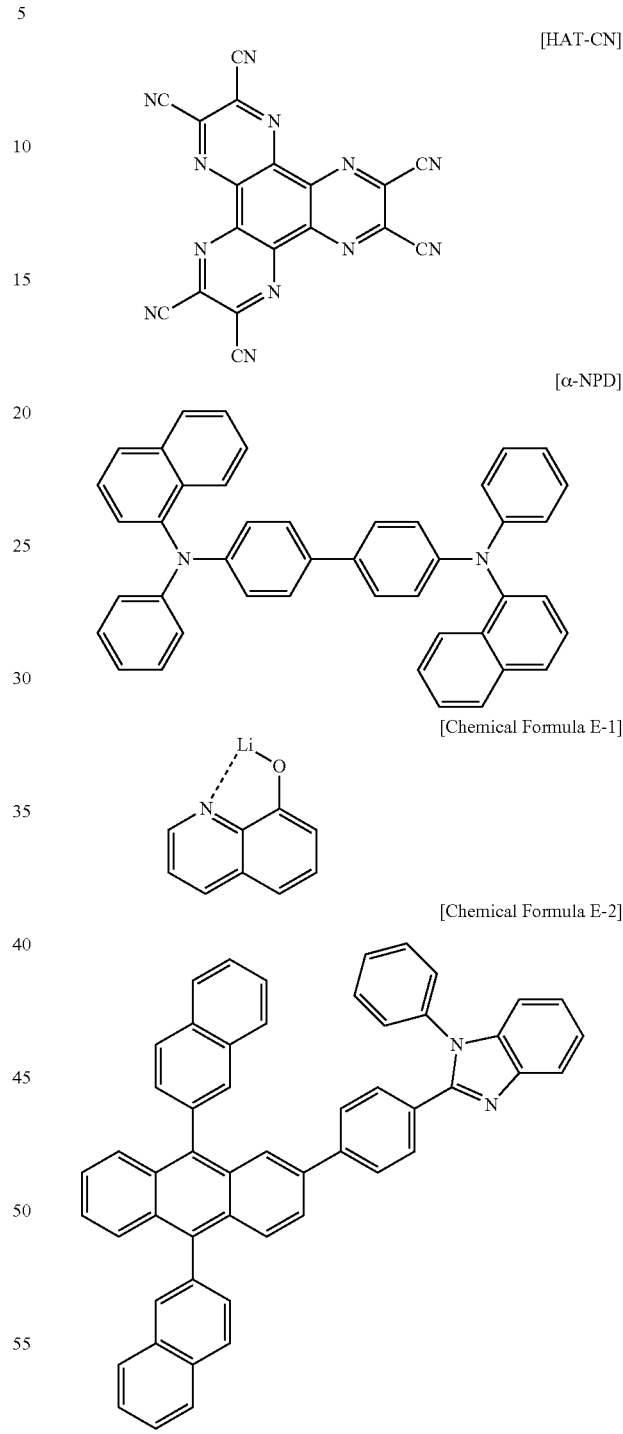

[HAT-CN]

[α-NPD]

[Chemical Formula E-1]

[Chemical Formula E-2]

Comparative Examples 1 and 2

Organic light-emitting diodes were fabricated in the same manner as in Examples 1 to 12, with the exception that [BD1], instead of the compounds used in Examples 1 to 12, was used. Luminescence properties of the organic light-emitting diodes were measured at 0.4 mA. Structures of [BD1], [BH1], and [BH2] are as follows.

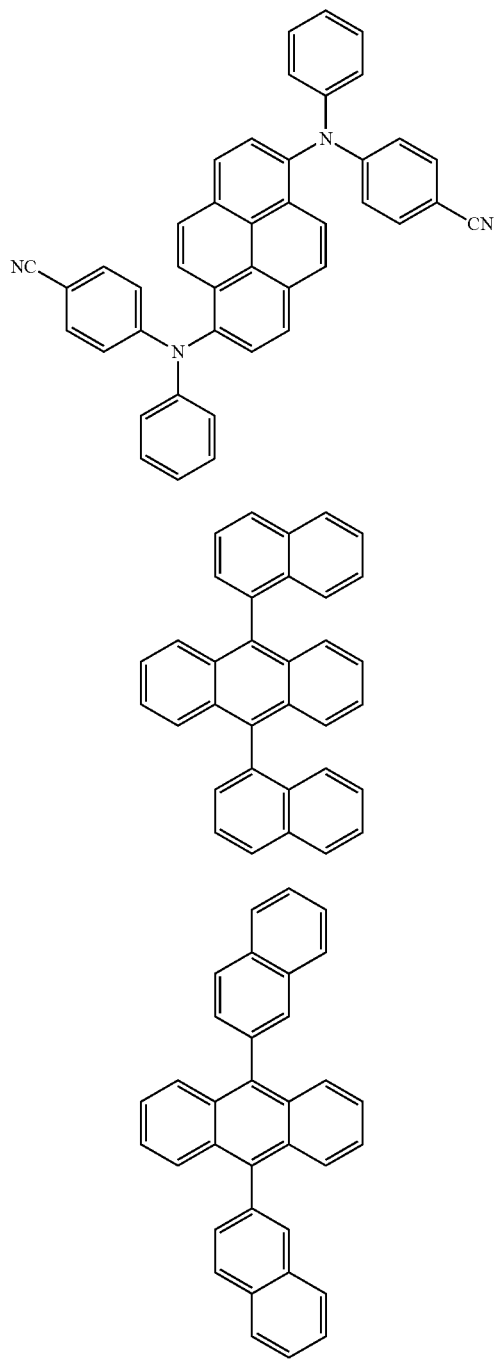

[BD1]

[BH1]

[BH2]

The organic light-emitting diodes fabricated in Examples 1 to 12 and Comparative Examples 1 and 2 were measured for voltage, luminance, color coordinate, and lifetime, and the results are summarized in Table 1, below. Voltages, luminance, and color coordinates were measured at a current density of 10 mA/cm$^2$, and T97 refers to a time taken for the initial luminance at a current density of 30 mA/cm$^2$ to decrease by 3%.

TABLE 1

| Ex. # | Dopant (Chemical Formula) | Host (Chemical Formula) | Potential (V) | Luminance (cd/m$^2$) | CIEx | CIEy | T97 (hr) |
|---|---|---|---|---|---|---|---|
| C. 1 | BD1 | BH1 | 4.0 | 454 | 0.140 | 0.087 | 15 |
| C. 2 | BD1 | BH2 | 4.0 | 448 | 0.141 | 0.090 | 13 |
| 1 | 1 | 33 | 3.8 | 550 | 0.143 | 0.073 | 87 |
| 2 | 1 | 24 | 3.7 | 530 | 0.146 | 0.069 | 105 |
| 3 | 4 | 24 | 3.7 | 538 | 0.145 | 0.071 | 101 |
| 4 | 4 | 24 | 3.7 | 538 | 0.145 | 0.071 | 101 |
| 5 | 5 | 25 | 3.8 | 581 | 0.143 | 0.079 | 67 |
| 6 | 5 | 29 | 3.8 | 607 | 0.142 | 0.083 | 120 |
| 7 | 7 | 23 | 3.8 | 548 | 0.145 | 0.070 | 77 |
| 8 | 7 | 24 | 3.7 | 534 | 0.147 | 0.067 | 105 |
| 9 | 9 | 31 | 3.8 | 590 | 0.146 | 0.069 | 55 |
| 10 | 9 | 24 | 3.7 | 534 | 0.147 | 0.067 | 105 |
| 11 | 16 | 52 | 3.4 | 552 | 0.143 | 0.074 | 47 |
| 12 | 16 | 58 | 3.6 | 539 | 0.142 | 0.075 | 99 |

As is understood from the data of Table 1, the organic light-emitting diodes of the present disclosure exhibited higher luminous efficiency in the deep blue range of CIEy≤0.1 and a longer lifetime than the conventional organic light-emitting diodes employing the compounds of Comparative Examples 1 and 2, thereby demonstrating their high applicability to organic electroluminescence devices.

Figure 2:
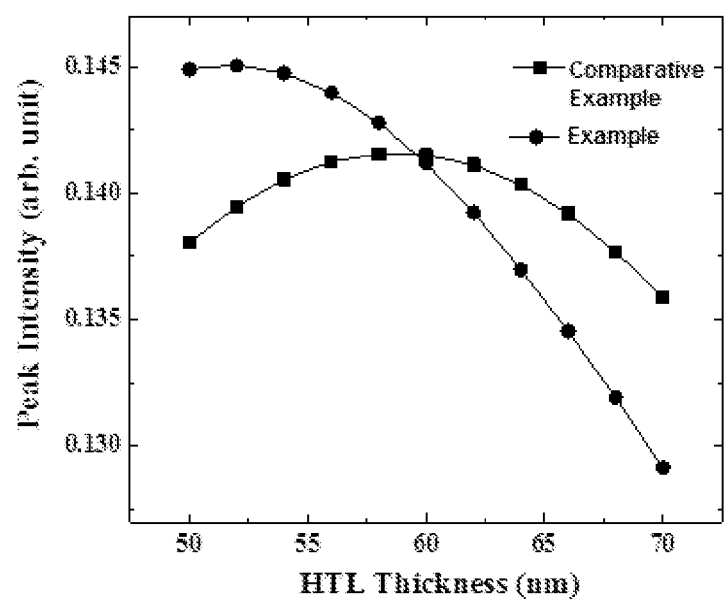
FIG. 2 shows efficiencies of an organic light-emitting diode according to an embodiment of the present disclosure with the thickness of HTL, as simulated in comparison with a comparative example.

Referring to FIG. 2, efficiencies of an organic light-emitting diode of Example 1 are shown with the thickness of the hole transport layer (HTL), as simulated in comparison with a conventional organic light-emitting diode. The efficiency of the organic light-emitting diode of Comparative Example peaked at an HTL thickness of 60 nm whereas peak efficiency was detected at an HTL thickness of 52.5 nm in the organic light-emitting diode of Example 1.

That is, considering the simulation results, the use of deep blue materials having a CIEy of 0.1 or less allows for maximum luminous efficiency even at a smaller thickness of the hole transport layer (HTL), and enables the expectation of low-voltage driving and enhanced current efficiency as the smaller thickness accounts for a shorter path that the injected holes travel.

Further, the thin HLT gives the additional advantage of reducing the fabrication processes of organic light-emitting diodes and the production cost.

Figure 3:
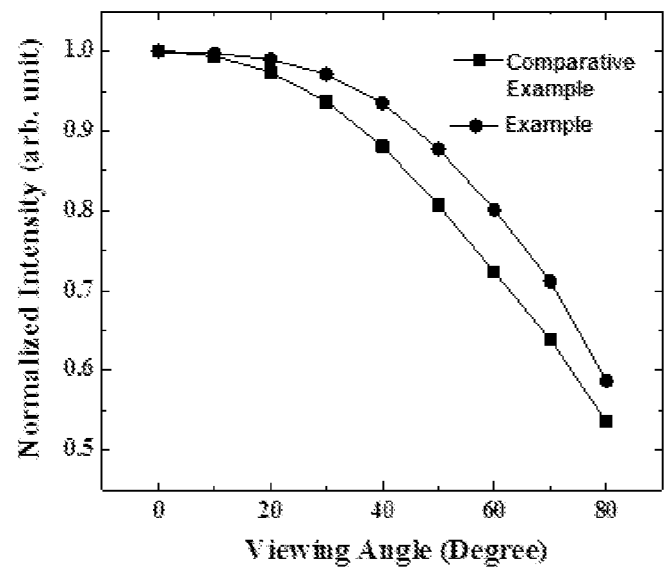
FIG. 3 shows viewing angles of an organic light-emitting diode according to an embodiment of the present disclosure, in comparison with an organic light-emitting diode of Comparative Example 1.

FIG. 3 shows viewing angles of an organic light-emitting diode of Example 1, in comparison with an organic light-emitting diode of Comparative Example 1. As can be seen, the organic light-emitting diode according to the present disclosure maintained higher luminous intensity even at a viewing angle of up to 60°, compared to the conventional organic light-emitting diode. Given the luminescent materials of the present disclosure, the organic light-emitting diodes can guarantee enhanced color reproducibility according to viewing angles.

Figure 4:
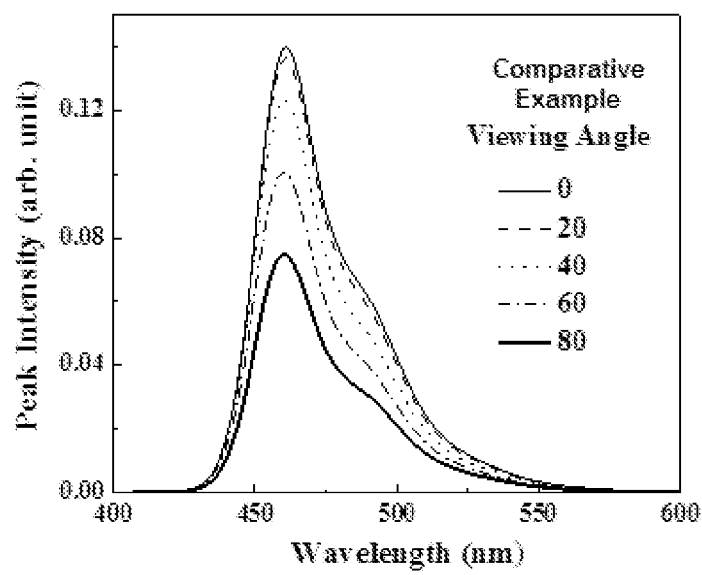
FIG. 4 shows spectra for peak intensity of an organic light-emitting diode of Comparative Example 1 according to viewing angles.
Figure 5:
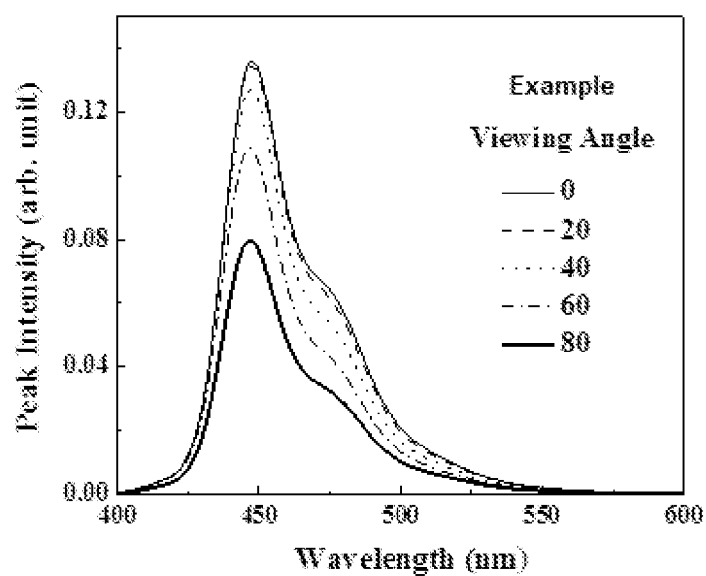
FIG. 5 shows spectra for peak intensity of an organic light-emitting diode of Example 1 according to viewing angles.

FIGS. 4 and 5 are spectra for peak intensity of organic light-emitting diodes of Comparative Example 1 and Example 1 according to viewing angles, respectively.

At general blue color coordinates (CIEy>0.1), light intensity significantly decreases with viewing angles. The emittance (EM) peak of an organic stack structure of organic light-emitting diodes is small in FWHM (Full Width Half Maximum) at a blue wavelength band, and tends to shift toward short wavelengths according to viewing angles. The lumeniscence intensity decreases with viewing anges because an overlap area between an EM peak in a blue wavelength band and a blue PL spectrum is reduced with the increasing of viewing angles.

As can be seen in FIG. 5, the use of deep blue materials having a CIEy of 0.1 or less deters the attenuation of luminescence intensity in the blue wavelength band even at a large viewing angle. These simulation results support the aforementioned description.

As described hitherto, the organic light-emitting diode according to the present disclosure can emit deep blue light at a color coordingate CIEy on a chromaticity diagram of 0.1 or less at higher efficiency with a longer lifetime, compared to conventional organic light-emitting diodes.

In the organic light-emitting diode emitting deep blue light with a long lifetime in accordance with the present disclosure, the common layer of an organic light-emitting diode, particularly a hole transport layer and/or a hole injection layer can be formed at a smaller thickness, resulting in an economical benefit in the stacking of the organic light-emitting diodes as well as an additional advantage of enabling low-voltage driving thanks to the thin layer.

Further, the organic light-emitting diode according to the present disclosure can give a wide viewing angle and bring about an improvement in color reproductively, compared to conventional techniques.

Although the embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An organic light-emitting diode, comprising:
   a first electrode;
   a second electrode facing the first electrode; and
   an emissive layer intercalated between the first electrode and the second electrode, wherein the emissive layer comprises at least one of the amine compounds represented by the following Chemical Formula A, and emits light with a color coordinate CIEy on a chromaticity diagram of 0.1 or less:

[Chemical Formula A]

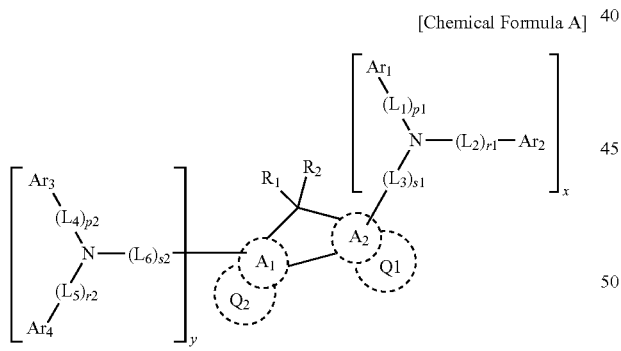

wherein $Q_1$ is

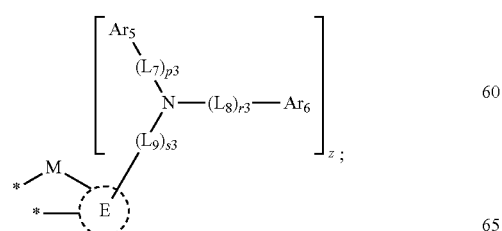

$Q_2$ is

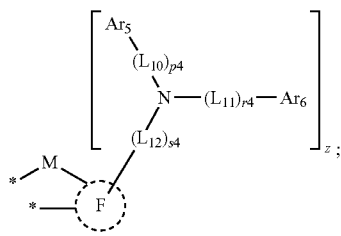

$A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substitutents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with a proviso that $R_1$ and $R_2$ together may form a mono- or polycyclic aliphatic or aromatic ring that may be a heterocyclic ring with a heteroatom selected from among N, O, P, Si, S, Ge, Se, and Te as a ring member;

p1 to p4, r1 to r4, and s1 to s4 are each independently an integer of 1 to 3, with a proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the A1 ring occupy respective positions * of $Q_2$ to form a fused ring, and two adjacent carbon atoms of the $A_2$ ring occupy respective positions * of $Q_1$ to form a fused ring, the term 'substituted' in the expression 'substituted or unsubstituted' is to have a substituent selected from the group consisting of deuterium, cyano, halogen, hydroxy, nitro, alkyl of 1 to 24 carbon atoms, halogenated alkyl of 1 to 24 carbon atoms, alkenyl of 2 to 24 carbon atoms, alkynyl of 2 to 24 carbon atoms, heteroalkyl of 1 to 24 carbon atoms, aryl of 6 to 24 carbon atoms, arylalkyl of 7 to 24 carbon atoms, heteroaryl of 2 to 24 carbon atoms or heteroarylalkyl of 2 to 24 carbon atoms, alkoxy of 1 to 24 carbon atoms, alkylamino of 1 to 24 carbon atoms, arylamino of 6 to 24 carbon atoms, hetero arylamino of 1 to 24 carbon atoms, alkylsilyl of 1 to 24 carbon atoms, arylsilyl of 6 to 24 carbon atoms, and aryloxy of 6 to 24 carbon atoms.

2. The organic light-emitting diode of claim 1, wherein the emissive layer comprises a host and a dopant, and the amine compound of Chemical Formula A serves as the dopant.

3. The organic light-emitting diode of claim 2, wherein the emissive layer includes as a host an anthracene derivative represented by the following Chemical Formula B:

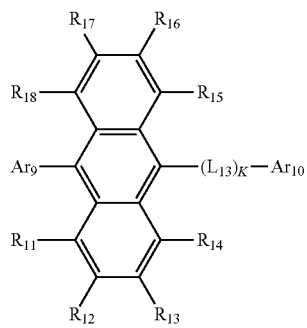

[Chemical Formula B]

wherein $R_{11}$ to $R_{18}$ may be the same or different, and are the same as above defined for $R_1$ to $R_9$;

$Ar_9$, and $Ar_{10}$ may be the same or different and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms;

$L_{13}$ represents a direct bond, or is a substituted or unsubstituted arylene of 6 to 20 carbon atoms or a substituted or unsubstituted heteroarylene of 2 to 20 carbon atoms; and k is an integer of 1 to 3, with a proviso that when k is 2 or greater, the corresponding linkers L13 may be the same or different.

4. The organic light-emitting diode of claim 3, wherein the substituent Arg of Chemical Formula B is represented by the following Chemical Formula C-1:

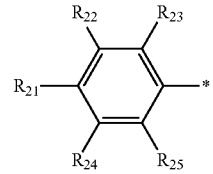

[Chemical Formula C-1]

wherein, $R_{21}$ to $R_{25}$ may be the same or different and are each the same as above defined for $R_1$ to $R_9$, and an adjacent two of them may be bonded to each other to form a saturate or unsaturated ring.

5. The organic light-emitting diode of claim 4, wherein L13 represents a direct bond or a substituted or unsubstituted arylene of 6 to 20 carbon atoms, and k is an integer of 1 to 2, with a proviso that when k is 2, the corresponding linkers L13 may be the same or different.

6. The organic light-emitting diode of claim 3, wherein the anthracene derivative is one selected from among compounds represented by the following Chemical Formula 22 to Chemical Formula 60:

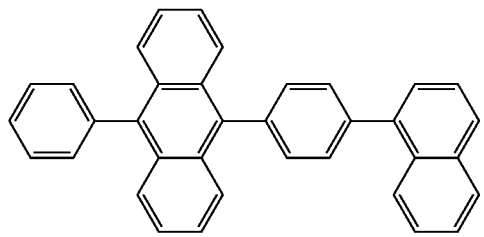

<22>

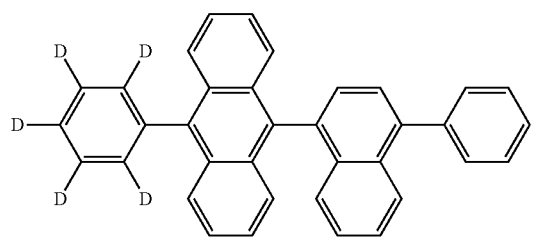

<23>

-continued
<24>
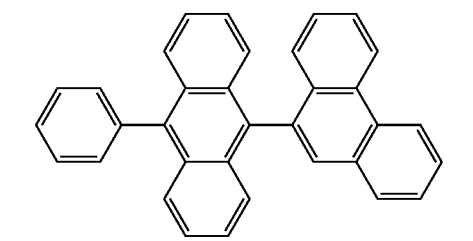
<25>
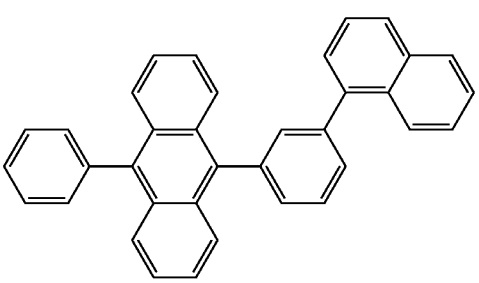
<26>
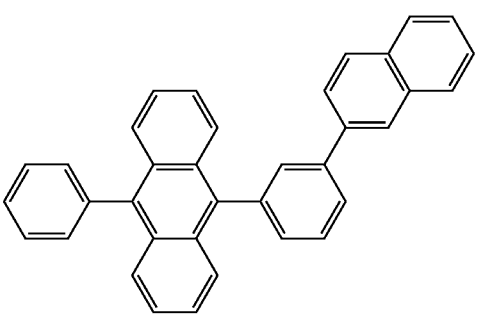
<27>
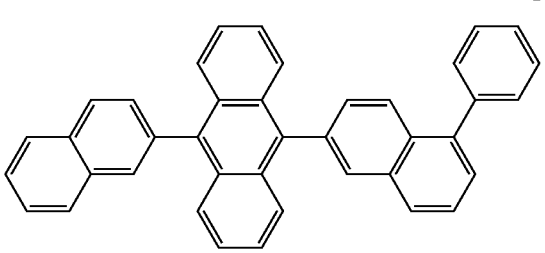
<28>
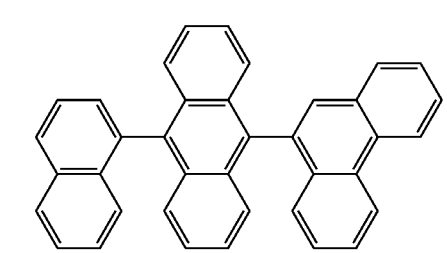
<29>
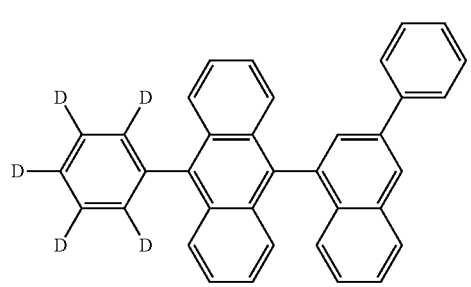
-continued
<30>
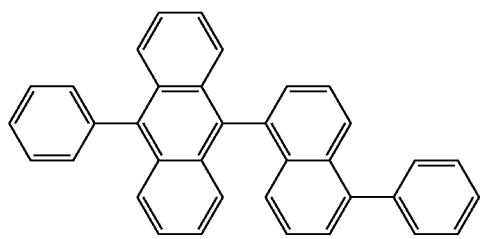
<31>
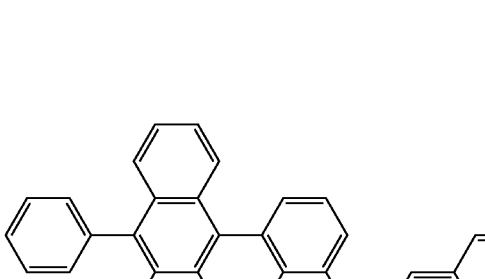
<32>
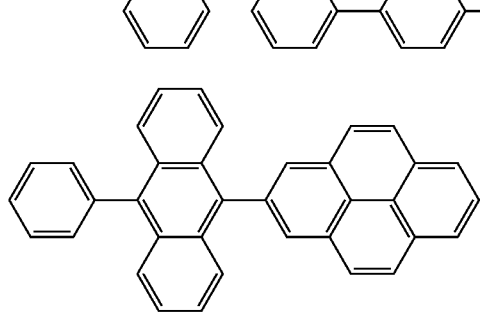
<33>
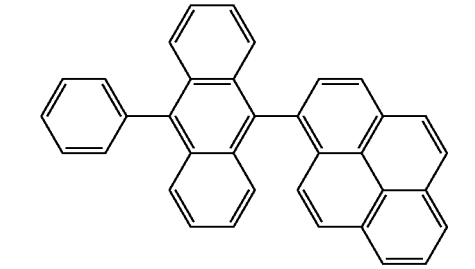
<34>
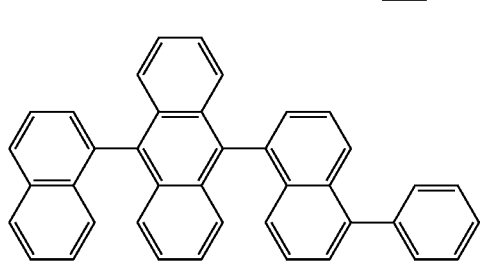
<35>
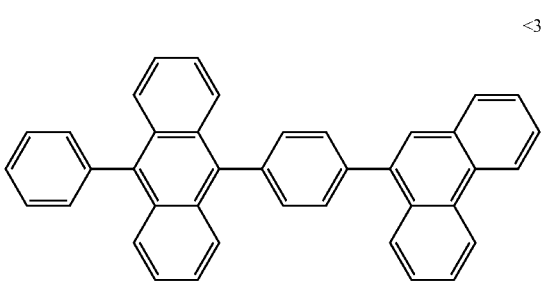

<36>
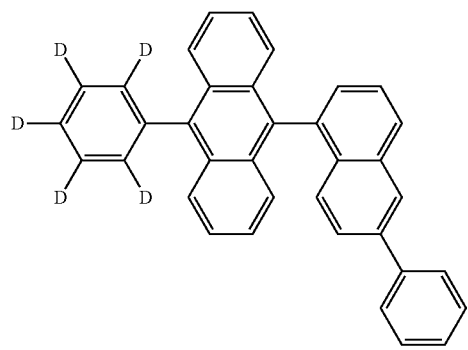
<37>
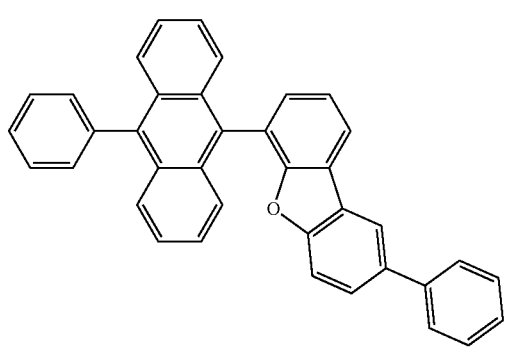
<41>
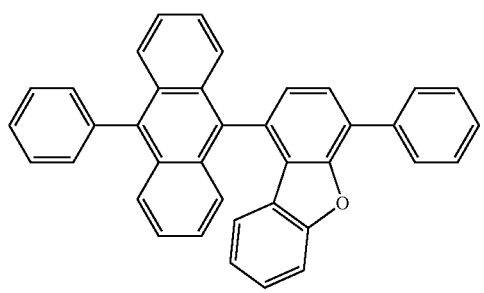
<42>
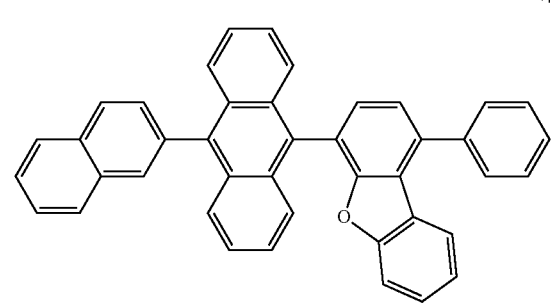
<38>
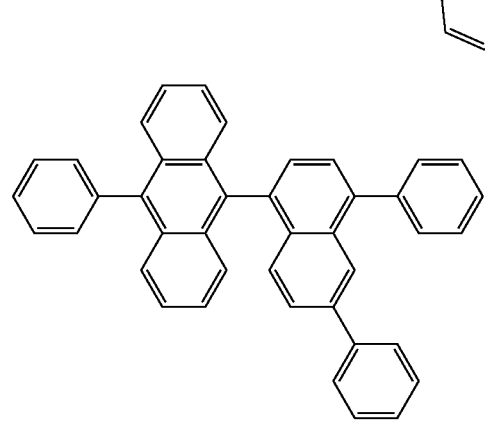
<43>
<44>
<39>
<40>
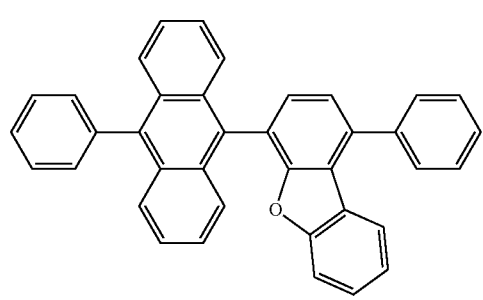
<45>
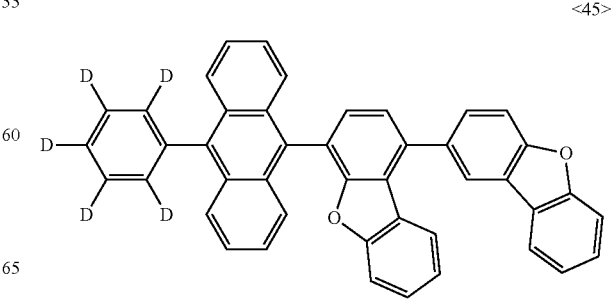

-continued
<46>
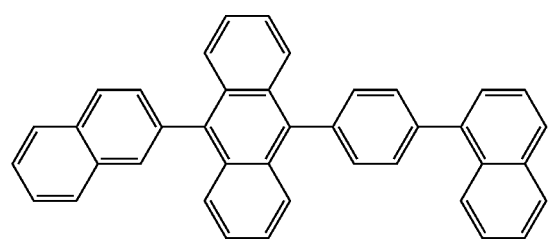
<47>
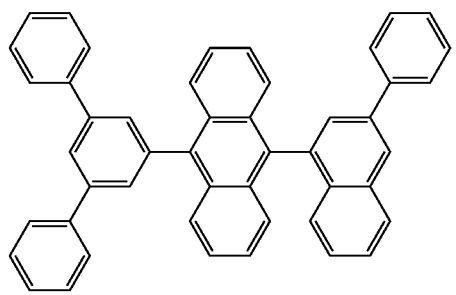
<48>
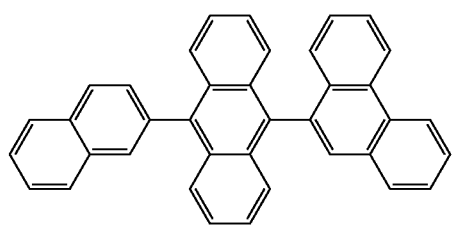
<49>
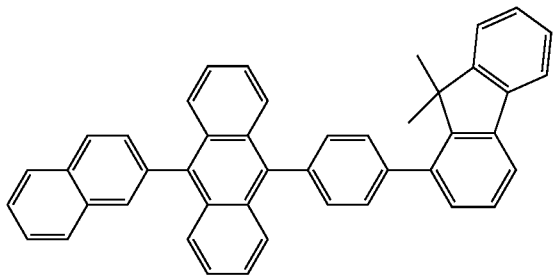
<50>
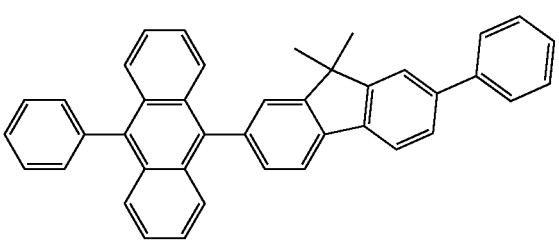
<51>
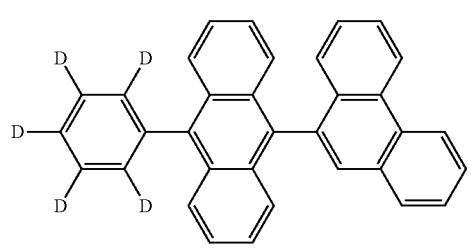
-continued
<52>
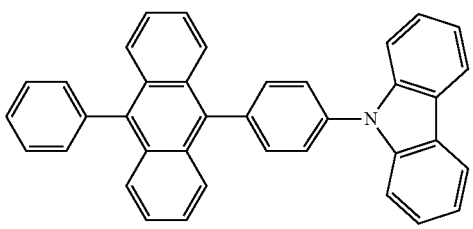
<53>
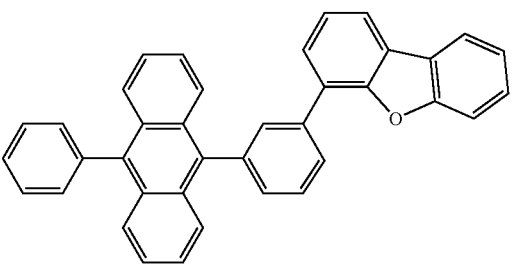
<54>
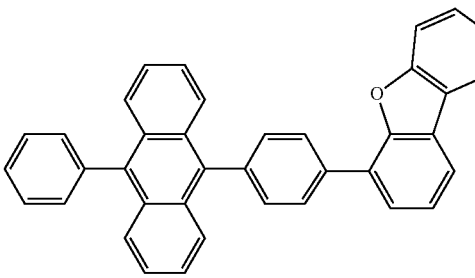
<55>
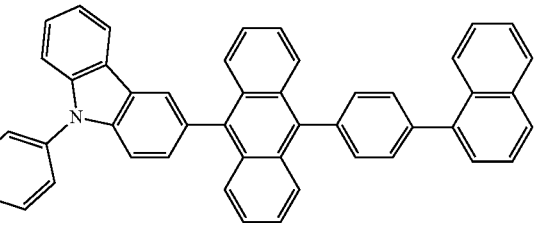
<56>
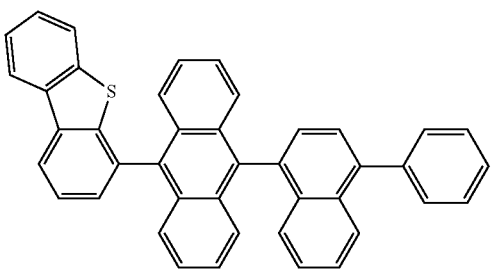
<57>
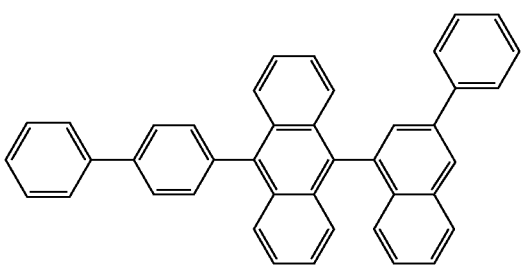

-continued

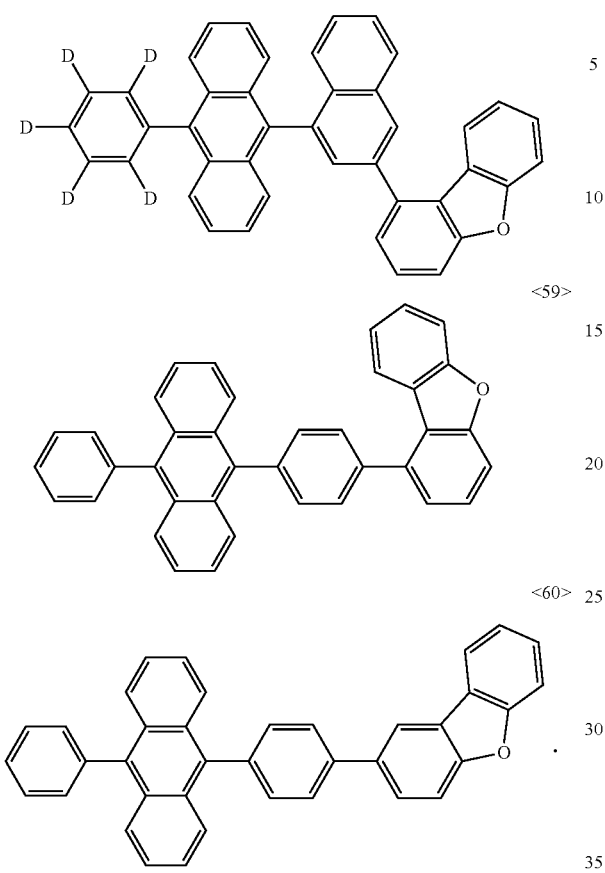

<58>

<59>

<60>

7. The organic light-emitting diode of claim 1, wherein A1, A2, E, and F of Chemical Formula A may be identical or different, and are each independently a substituted or unsubstituted aromatic hydrocarbon ring of 6 to 50 carbon atoms.

8. The organic light-emitting diode of claim 7, wherein the substituted or unsubstituted aromatic hydrocarbon ring of 6 to 50 carbon atoms is selected from among compounds represented by Structural Formula 10 to Structural Formula 21:

[10]

[11]

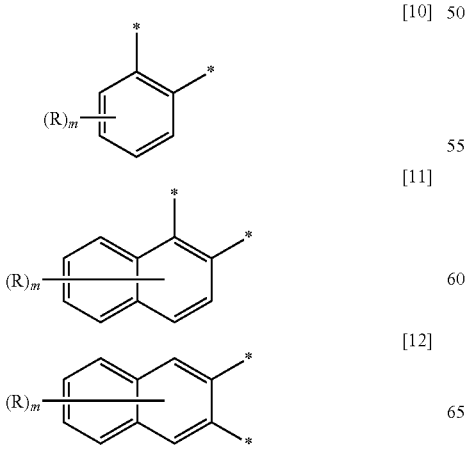

[12]

-continued

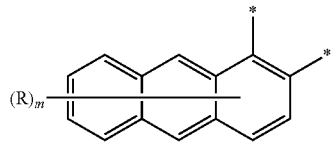

[13]

[14]

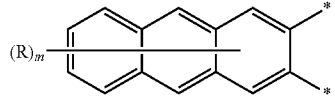

[15]

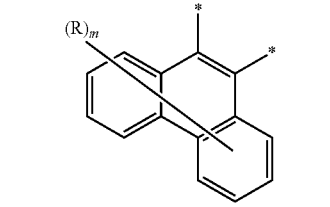

[16]

[17]

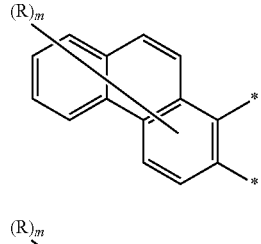

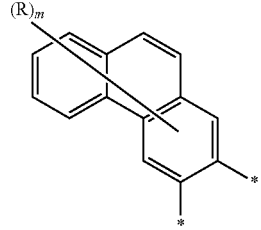

[18]

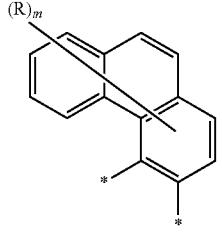

[19]

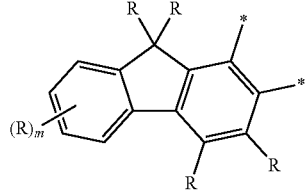

[20]

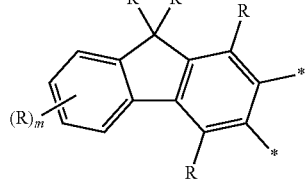

-continued

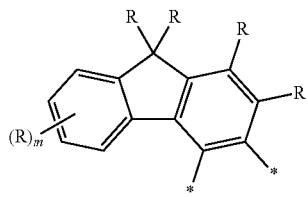
[21]

wherein, "-*" for moiety $A_1$ or $A_2$ denotes a bonding site for forming a 5-membered ring containing the carbon atom connected to both the substituents $R_1$ and $R_2$, and "-*" for moiety E or F denotes a bonding site for forming a 5-membered ring containing M of the structural Formula $Q_1$ and $Q_2$ with moiety $A_1$ or $A_2$, when one of the aromatic hydrocarbon rings of Structural Formula 10 to Structural Formula 21 for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R is the same as above defined for $R_1$ and $R_2$, and m is an integer of 1 to 8, with a proviso that when m is 2 or greater, or R is 2 or greater, the corresponding Rs may be the same or different.

9. The organic light-emitting diode of claim 1, wherein the linkers $L_1$ to $L_{12}$ in Chemical Formula A represent respective direct bonds, or are each any one selected from among a substituted or unsubstituted arylene of 6 to 20 carbon atoms and a substituted or unsubstituted heteroarylene of 2 to 20 carbon atoms.

10. The organic light-emitting diode of claim 9, wherein the linkers $L_1$ to $L_{12}$ represent respective direct bonds, or are each any one selected from the following Structural Formula 22 to Structural Formula 30, p1 to p4, r1 to r4, and s1 to s4 are each 1 or 2, and x is 1:

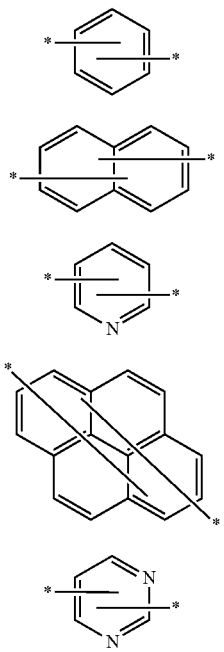
[22]
[23]
[24]
[25]
[26]

-continued

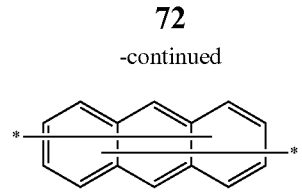
[27]
[28]

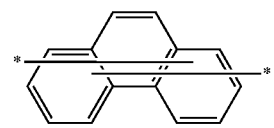
[29]

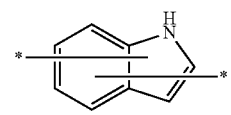
[30]

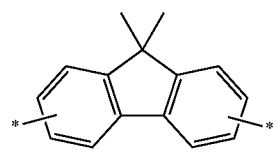

wherein hydrogen or deuterium may be positioned on a carbon atom as a member in the aromatic rings of the linkers.

11. The organic light-emitting diode of claim 1, wherein $R_1$ to $R_9$, and $Ar_1$ to $Ar_8$ may be the same or different and are each independently any one selected from among hydrogen, deuterium, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms containing at least one heteroatom selected from among O, N, S, and Si, a cyano, and a halogen.

12. The organic light-emitting diode of claim 1, wherein the amine compound is selected from the group consisting of the compounds represented by the following [Chemical Formula 1] to [Chemical Formula 21]:

<1>

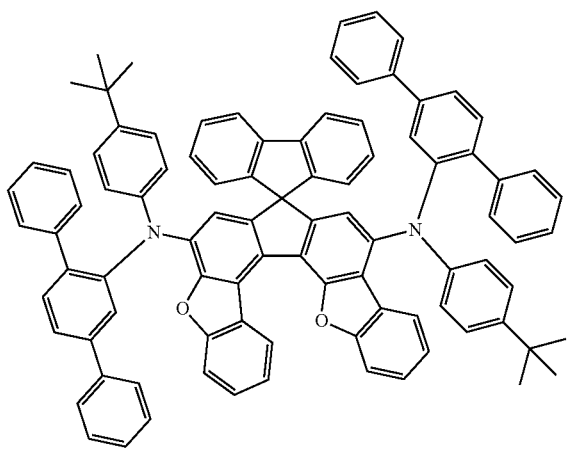

-continued
<2>
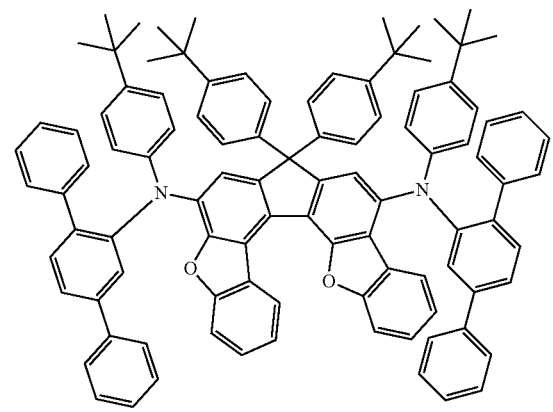
<3>
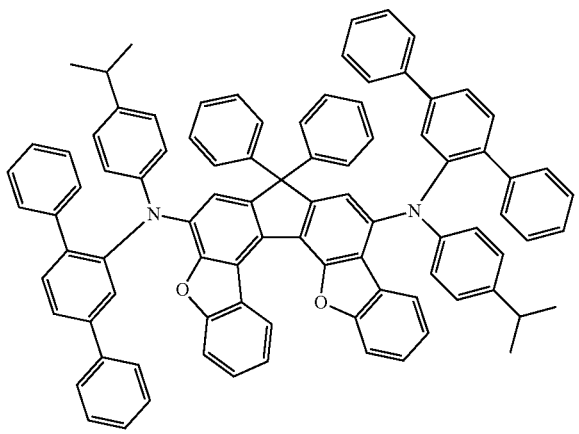
<4>
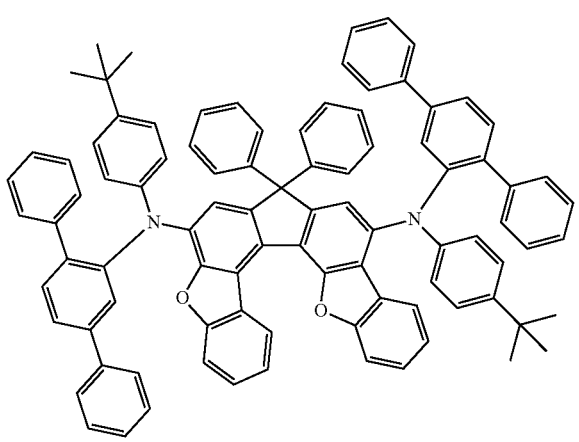
-continued
<5>
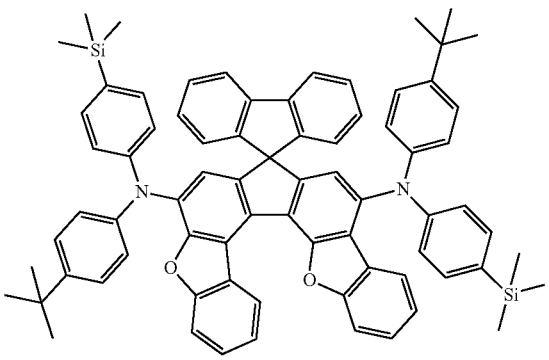
<6>
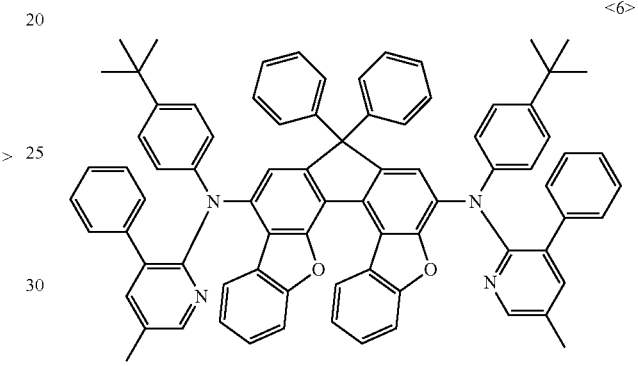
<7>
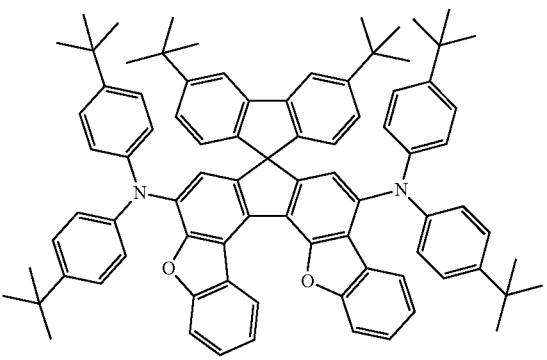
<8>
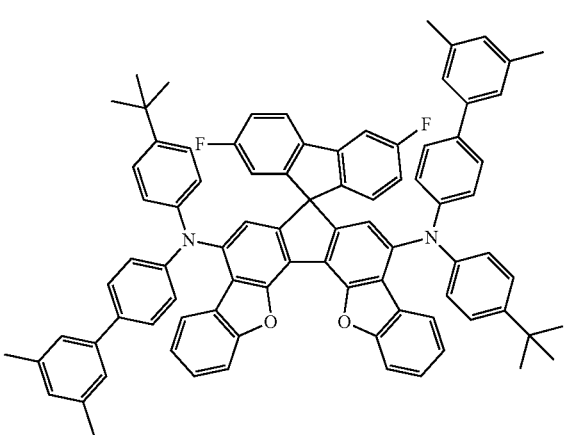

-continued
<9>
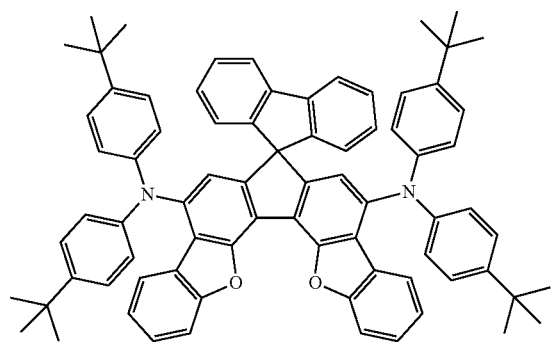
<10>
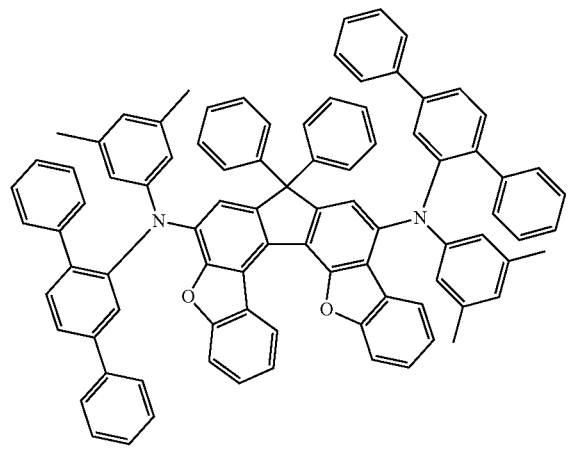
<11>
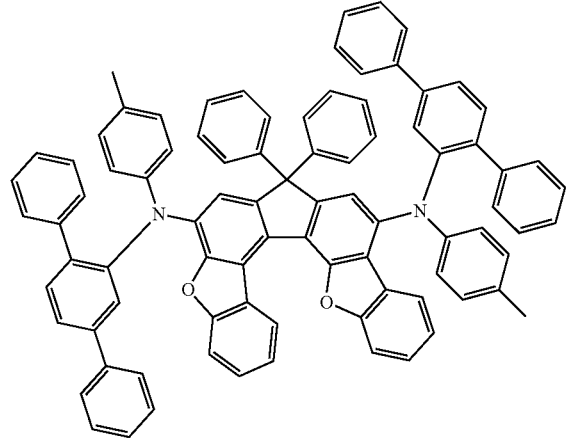
<12>
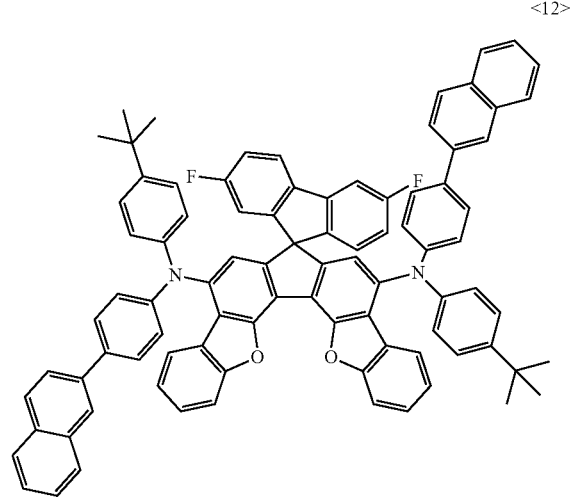
<13>
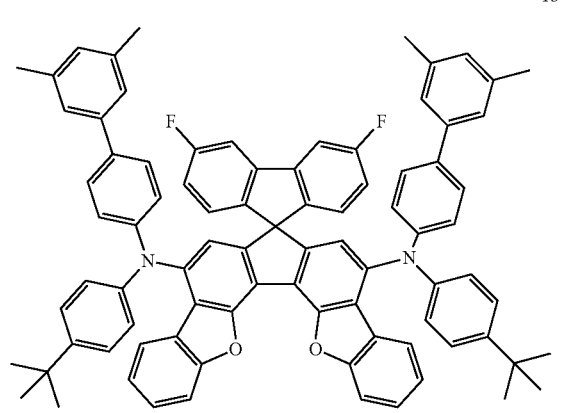
<14>
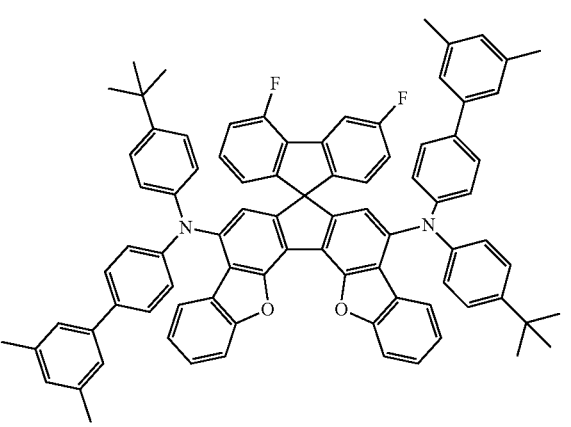

<15>

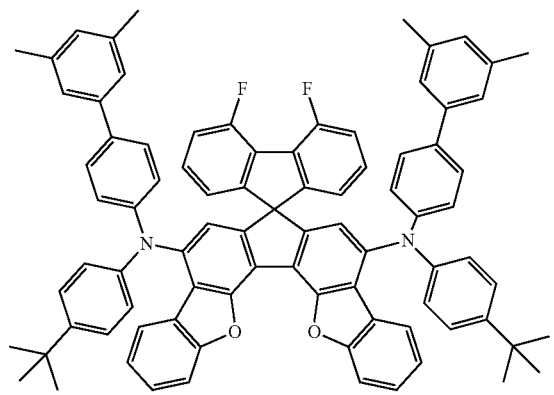

<16>

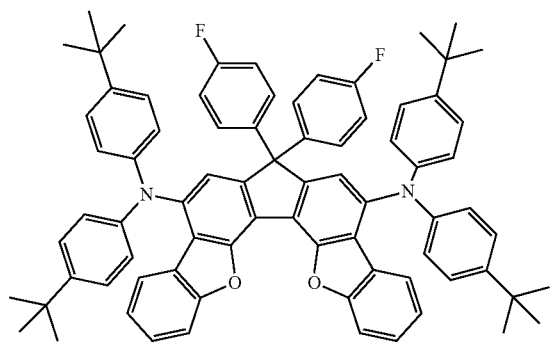

<17>

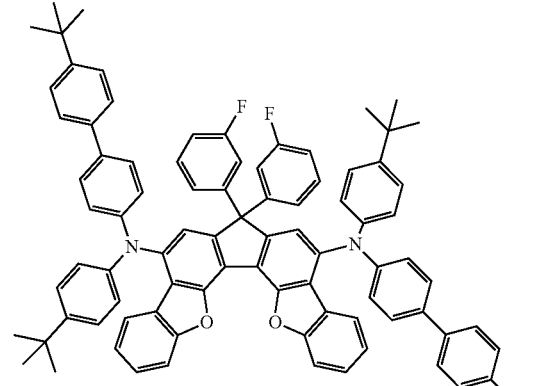

<18>

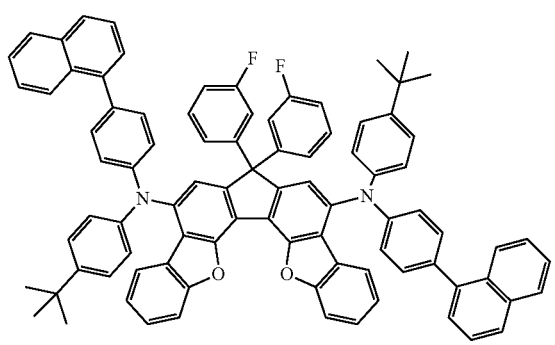

<19>

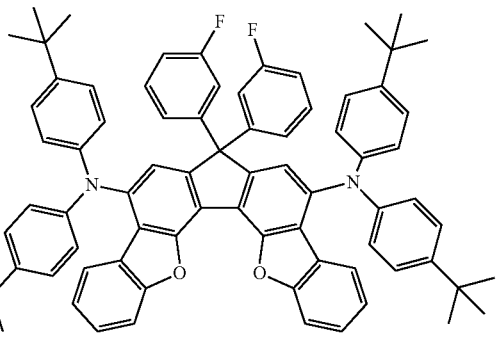

<20>

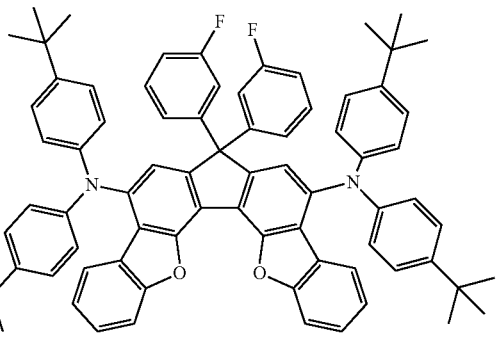

<21>

13. The organic light-emitting diode of claim 1, wherein the organic light-emitting diode comprises at least one of a hole injection layer, a hole transport layer, a functional layer capable of both hole injection and hole transport, an electron transport layer, and an electron injection layer, in addition to the emissive layer.

14. The organic light-emitting diode of claim 13, wherein at least one of the layers is formed using a deposition process or a solution process.

15. The organic light-emitting diode of claim 1, wherein the organic light-emitting diode comprises two or more emissive layers, the emissive layers including at least one layer employing a phosphorescent material and at least one layer employing the compound represented by Chemical Formula A.

16. The organic light-emitting diode of claim 15, wherein the phosphorescent material used in the emissive layer is a source of light with a mean wavelength of 550~620 nm.

17. The organic light-emitting diode of claim 1, wherein organic light-emitting diode is used for a device selected from among a flat display device, a flexible display device, a monochrome or white flat illumination device, and a monochrome or white flexible illumination device.

* * * * *